(12) United States Patent
Shin et al.

(10) Patent No.: US 6,436,960 B1
(45) Date of Patent: Aug. 20, 2002

(54) FARNESYL TRANSFERASE INHIBITORS HAVING A PIPERIDINE STRUCTURE AND PROCESS FOR PREPARATION THEREOF

(75) Inventors: You Seung Shin; Jong Sung Koh; Hyun Il Lee; Jin Ho Lee; Jong Hyun Kim; Hyun Ho Chung; Kwi Hwa Kim; Tae Hwan Kwak; Seong Gu Ro; In Ae Ahn; Tae Saeng Choi; Young Hoon Oh; Chung Mi Kim; Sun Hwa Lee; Hyun Sung Kim, all of Daejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/601,426

(22) PCT Filed: Feb. 1, 1999

(86) PCT No.: PCT/KR99/00051
§ 371 (c)(1),
(2), (4) Date: Aug. 1, 2000

(87) PCT Pub. No.: WO99/38862
PCT Pub. Date: Aug. 5, 1999

(30) Foreign Application Priority Data

Feb. 2, 1998 (KR) .............................................. 98-2776
Feb. 2, 1998 (KR) .............................................. 98-2777
Jul. 14, 1998 (KR) ............................................ 98-28340
Aug. 7, 1998 (KR) ............................................ 98-32150

(51) Int. Cl.$^7$ ..................... A61K 31/454; C07D 401/14
(52) U.S. Cl. ....................... 514/326; 546/210; 546/269; 546/152; 546/146; 544/129; 544/360; 514/235.8; 514/252; 514/307; 514/314

(58) Field of Search ................................. 514/326, 252, 514/235.8, 307, 314; 546/210, 209, 145, 152; 544/129, 360

(56) References Cited

U.S. PATENT DOCUMENTS 6,268,363 B1 * 7/2001 Lee et al. ................. 514/235.8

* cited by examiner

Primary Examiner—Charanjit S. Aulakh
(74) Attorney, Agent, or Firm—Peter F. Corless; John B. Alexander; Edwards & Angell

(57) ABSTRACT

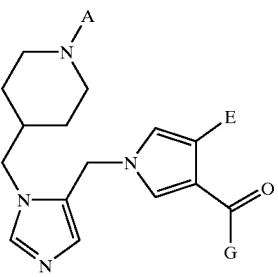

(1)

The present invention relates to a novel piperidine derivative represented by formula (1) which shows an inhibitory activity against farnesyl transferase or pharmaceutically acceptable salts thereof, in which A, E and G are defined in the specification; to a process for preparation of the compound of formula (1); to an intermediate which is used in the preparation of the compound of formula (1); and to a pharmaceutical composition comprising the compound of formula (1) as an active ingredient.

11 Claims, No Drawings

FARNESYL TRANSFERASE INHIBITORS HAVING A PIPERIDINE STRUCTURE AND PROCESS FOR PREPARATION THEREOF

This application is a 371 of PCT/KR99/00051 filed Feb. 1, 1999, now WO 99/38862.

TECHNICAL FIELD

The present invention relates to a novel piperidine derivative represented by the following formula (1) which shows an inhibitory activity against farnesyl transferase:

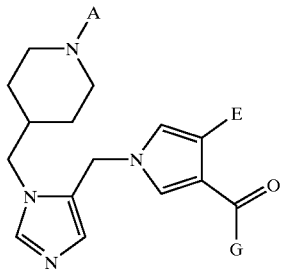

(1)

in which A, E and G are defined as described below, or pharmaceutically acceptable salts thereof.

The present invention also relates to a process for preparation of the compound of formula (1), to intermediates which are used in the preparation of the compound of formula (1), and to a pharmaceutical composition comprising the compound of formula (1) as an active ingredient.

BACKGROUND ART

Mammalian Ras proteins act as molecular switches in the signalling events associated with cell growth and differentiation. The ras proto-oncogene family consists of three members, N-, K-, and H-ras, which code for highly homologous 4 types of proteins; i.e., H, N-ras proteins of 189 residues and two isomorphic K-ras-4B and K-ras-4A proteins of 188 and 189 residues, respectively. The chemical basis for the switch mechanism involves cycling of the protein between the inactive (off) guanosine diphosphate (GDP) bound state and the active (on) guanosine triphosphate (GTP) bound state (Bourne, H. R.; Sanders, D. A.; McCormick. F.; Nature, 1991, 349, 117). Biochemical and structural studies have shown that point mutations of the residues 12, 13 and 61, positioned in the neighborhood of phosphoryl ground of GTP, resulting in the decrease of guanosine triphosphatase activity are associated with many human cancers, particularly, pancreatic cancer, urinary bladder carcinoma, colon cancer, etc. (Bos, J. L., Cancer Res., 1989, 49, 4682).

Ras protein is synthesized as a cytosolic precursor that ultimately localized to the cytoplasmic face of the plasma membrane after a series of posttranslational modification (Gibbs, J. B., Cell 1991, 65, 1). These series of biochemical modifications, by changing the electrical charge state or spacial structure to increase the hydrophobicity allow Ras protein to attach to cell membrane more easily. The first and obligatory step in the series is the addition of a farnesyl moiety to the cysteine residue of the C-terminal CAAX motif (C, cysteine; A, usually aliphatic residue; X, any other amino acid) in a reaction catalyzed by farnesyl protein transferase (FTase). This modification is essential for Ras function, as demonstrated by the inability of Ras mutants lacking the C-terminal cysteine to be farnesylated, to localize to the plasma, and to transform mammalian cells in culture (Hancock, J. F., Magee, A. I., Childs, J. E., Marshall, C. J., Cell 1989, 57, 1167). The subsequent posttranslational modifications, cleavage of the AAX residues, carboxyl methylation of the the farnesylated cysteine, and palmitoylation of the cysteines located upstream of the CAAX motif in H- and N-ras proteins are not obligatory for Ras membrane. association or cellular transforming activity. Interestingly, K-ras-4B, different from H- and N-ras, has a multiple lysine rich region named polybasic domain, instead of having cysteine required for palmitoylation, thereby facilitating the farnesylated ras protein to bind to anionic lipid layer of cell membrane. The inhibitors of FTase that catalyzes the obligatory modification have therefore been suggested as anticancer agents for tumors in which Ras oncogene contributes to transformation (Buses, J. E. et al., Chemistry & Biology, 1995, 2, 787). A number of FTase inhibitors recently identified demonstrated potent and specific ability to block Ras farnesylation, signalling and transformation in transformed cells and tumor cell lines both in vitro and in animal models (Kohl. N. E. et. al., Proc. Natl. Acad. Sci. USA. 1994, 91, 9141; Kohl, N. E. et al., Nature Medicine, 1995, 1 792).

However, most of the inhibitors are related to CAAX motif as Ras substrate mimic and peptidic in nature or contain a sulfhydryl group (U.S. Pat. No. 5,141,851; Kohl, N. E. et. al., Science, 1993, 260, 1934; PCT/US95/12224, Graham et al.; Sebti S. M. et. al., J. Biol. Chem., 1995. 270, 26802; James, G. L. et al., Science, 1993, 260, 1937; Bishop, W. R. et al., J. Biol. Chem., 1995, 270, 30611). Recently, a new type of peptidomimetic inhibitor imitating catalytic step of FTase has been reported (Poulter, C. D. et al., J. Am. Chem. Soc., 1996, 118, 8761). The chemical basis of the inhibitor design relates to the reaction mechanism. This is, transferring prenyl group by the enzyme is electrophilic displacement and the reaction requires (+) charge in a transition state.

These inhibitors previously described however possess limited activity and selectivity for inhibition of the oncogenic function of Ras proteins, particularly K-ras-4B, which is found to be most common in human cancer. Therefore, new inhibitor having the ability of effectively inhibiting K-ras activity is required.

With regard to the restenosis and vascular proliferative diseases, it has been shown that inhibition of cellular ras prevents smooth muscle proliferation after vascular injury in vivo (Indolfi C. et al., Nature Med., 1995, 1(6), 541–545). This report definitively supports a role for farnesyl transferase inhibitors in this disease, showing inhibition of accumulation and proliferation of vascular smooth muscle.

DISCLOSURE OF INVENTION

The present inventors have performed studies for developing a compound having the structure characteristics imitating an intermediate state of catalytic reaction of FTase and as a result, found that piperidine derivatives according to the present invention can potently inhibit the enzyme.

Therefore, the object of the present invention is to provide a piperidine derivative of formula (1) which inhibits the activity of FTase, process for preparation thereof, and a novel intermediate which can be used effectively in the process for preparing the compound of formula (1).

It is another object of the present invention to provide a pharmaceutical composition comprising the compound of formula (1) as an active ingredient.

BEST MODE FOR CARRYING OUT THE INVENTION

It is the first object of the present invention to provide a piperidine derivative represented by the following formula (1) and pharmaceutically acceptable salts thereof which inhibit the activity of farnesyl transferase:

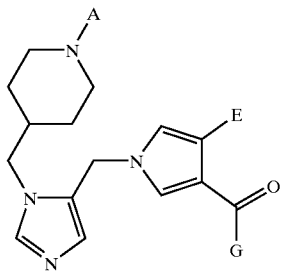

(1)

in which
A represents hydrogen, lower alkyl, or

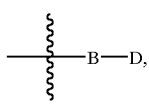

wherein
B represents $CH_2$, C=O or $SO_2$, and
D represents a radical selected from the following group:

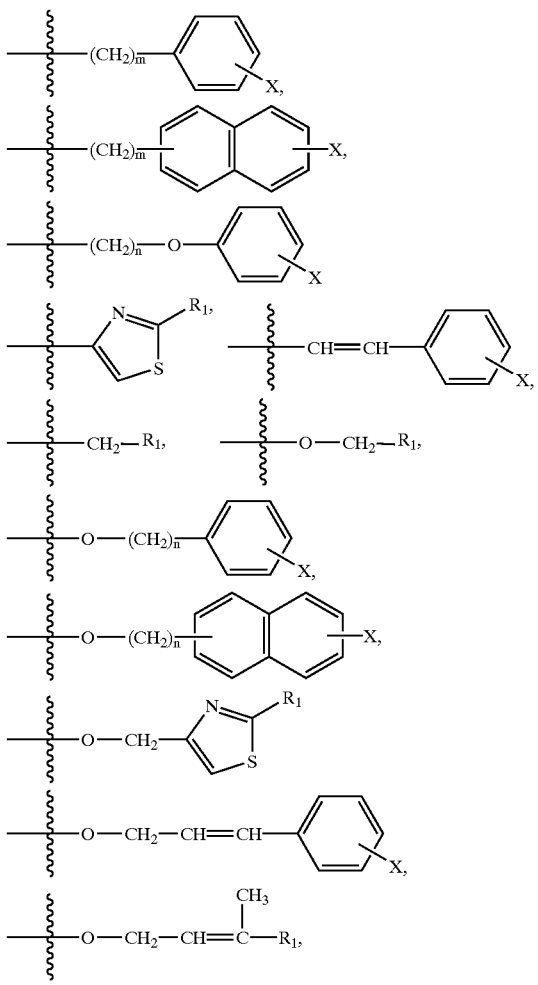

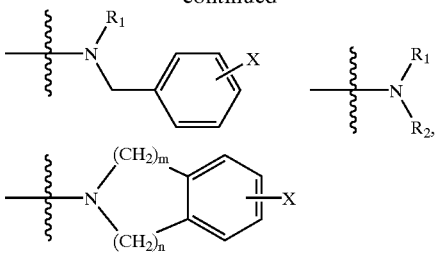

In the definition for the substituent D,
m denotes an integer of 0 to 3,
n denotes an integer of 1 to 3,
X represents hydrogen, phenyl, phenoxy, lower alkyl, lower alkoxy, halogen, nitro, or amino which is optionally substituted by benzyl or lower alkyl,
$R_1$ and $R_2$ independently of one another represent hydrogen, lower alkyl, $C_3$–$C_6$-cycloalkyl, lower alkyl substituted by $C_3$–$C_6$-cycloalkyl, aryl or heteroaryl,
E represents hydrogen, phenyl, naphthyl or

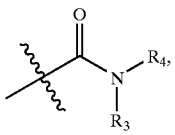

wherein
$R_3$ and $R_4$ independently of one another represent hydrogen, lower alkyl, aryl or

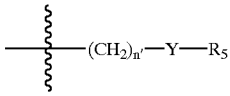

(wherein Y represents O or S, n' denotes an integer of 2 to 4, and $R_5$ represents lower alkyl),
G represents a radical selected from the following group:

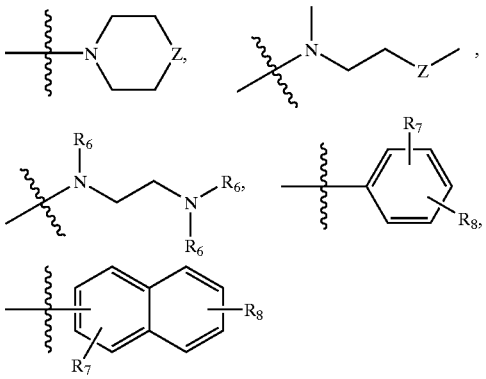

wherein
Z represents O, S, $SO_2$ or N—$R_6$ (wherein $R_6$ represents hydrogen or lower alkyl),
$R_7$ and $R_8$ independently of one another represent hydrogen, lower alkyl, lower alkoxy, halogen, cyano, hydroxycarbonyl, aminocarbonyl, aminothiocarbonyl, hydroxy, phenyl or phenoxy.
Particularly, the compound according to the present invention has a quite different structure from the known inhibitors for farnesyl transferase, and furthermore it does never include the thiol moiety.

In the definitions for the substituents of the compound of formula (1), the term "lower alkyl" means a straight-chain or branched alkyl having 1 to 4 carbon atoms which includes methyl, ethyl, isopropyl, isobutyl and t-butyl; the term "cycloalkyl" means cyclic alkyl which includes cyclohexyl; the term "aryl" means 6 to 14-membered monocyclic-, bicyclic- or tricyclic aromatic group; and the term "heteroaryl" means 6 to 14-membered monocyclic-, bicyclic- or tricyclic aromatic group containing hetero atom(s) selected from a group consisting of oxygen, nitrogen and sulfur.

Also, the compound of formula (1) according to the present invention can form a pharmaceutically acceptable salt. Such salt includes non-toxic acid addition salt containing pharmaceutically acceptable anion, for example a salt with inorganic acids such as hydrochloric acid, sulfuric acid, nitric acid, phosphoric acid, hydrobromic acid, hydriodic acid, etc., a salt with organic carboxylic acids such as tartaric acid, formic acid, citric acid, acetic acid, trichloroacetic acid, trofluoroacetic acid, gluconic acid, benzoic acid, lactic acid, fumaric acid, maleic acid, aspargic acid, etc., or a salt with sulfonic acids such as methanesulfonic acid, benzenesulfonic acid, p-toluenesulfonic acid, naphthalenesulfonic acid, etc.; base addition salt for example a salt with pyridine or ammonia; and metal addition salt for example a salt with alkali metal or alkaline earth metal such as lithium salt. Further, the present invention includes a solvate of the compound of formula (1) such as alcoholate or hydrate thereof. They can be produced by conventional conversion methods.

Among the compound of formula (1) according to the present invention, the preferred compounds include those wherein A represents hydrogen, lower alkyl, or

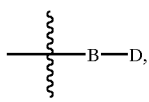

wherein

B represents $CH_2$, $C=O$ or $SO_2$,

D represents a radical selected from the following group:

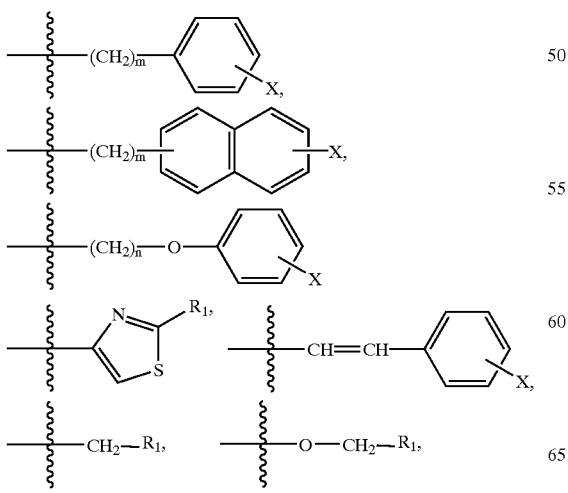

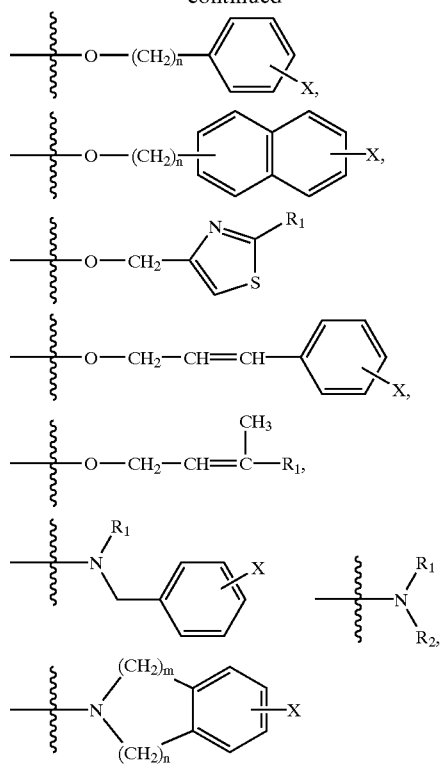

In the definition for the substituent D, m denotes an integer of 0 to 1, n denotes an integer of 1 to 2, X represents hydrogen, $R_1$ and $R_2$ independently of one another represent hydrogen or lower alkyl, E represents hydrogen, phenyl, naphthyl, or

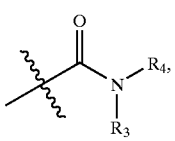

wherein $R_3$ and $R_4$ independently of one another represent hydrogen, lower alkyl, or 2-methoxyethyl, G represents a radical selected from the following group:

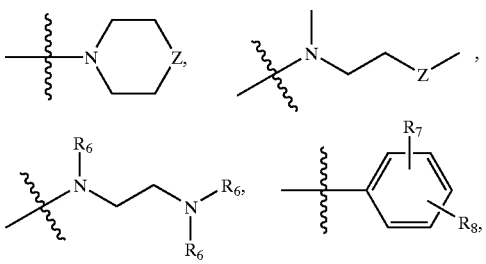

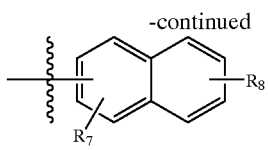
wherein
Z represents O or N—$R_6$ (wherein $R_6$ represents methyl),
$R_7$ and $R_8$ independently of one another represent hydrogen.
Typical examples of the compound of formula (1) according to the present invention are presented in the following Table 1.
TABLE 1-1
| COM. NO. | STRUCTURE |
|---|---|
| 1 | 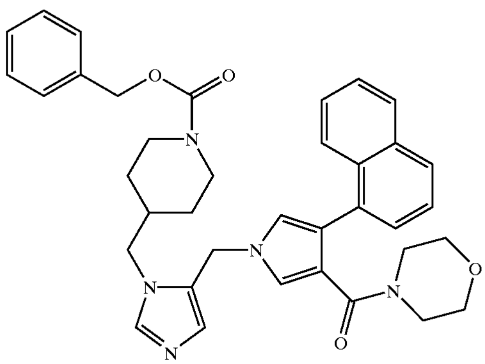 |
| 2 | 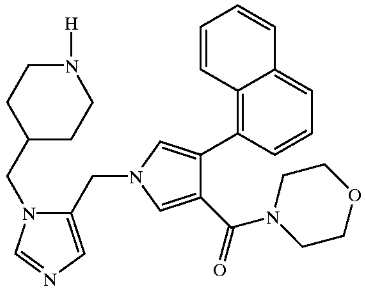 |
| 3 | 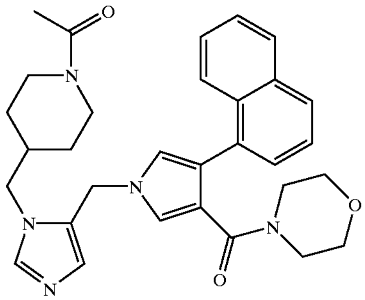 |
TABLE 1-1-continued
| COM. NO. | STRUCTURE |
|---|---|
| 4 | 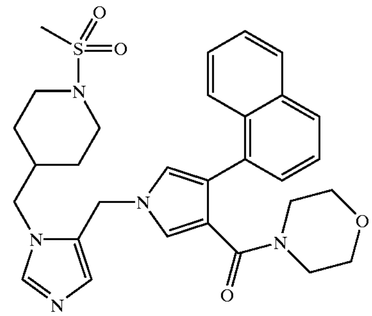 |
| 5 | 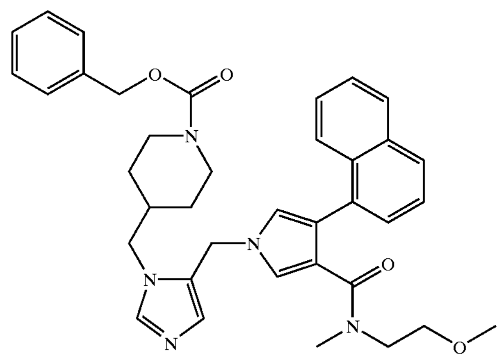 |
| 6 | 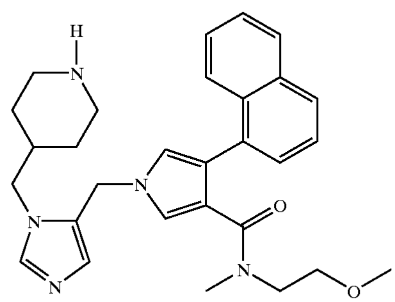 |
| 7 | 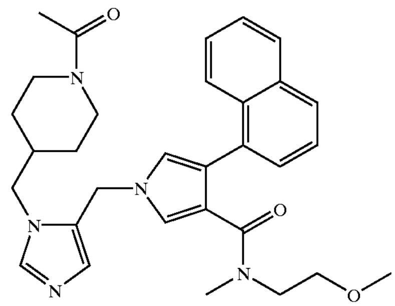 |

TABLE 1-1-continued

| COM. NO. | STRUCTURE |
|---|---|
| 8 | 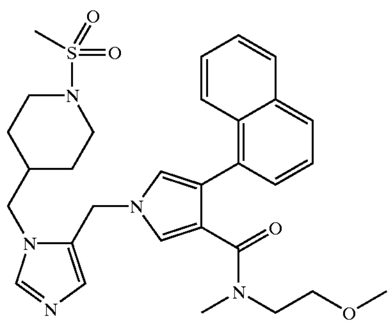 |

TABLE 1-2

| COM. NO. | STRUCTURE |
|---|---|
| 9 | 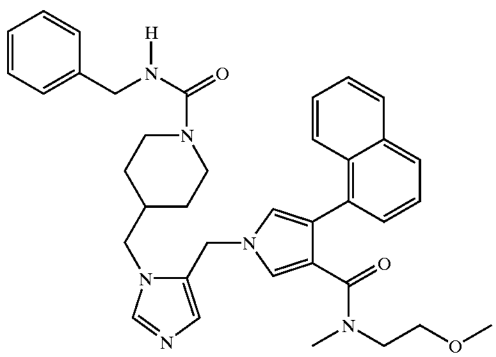 |
| 10 | 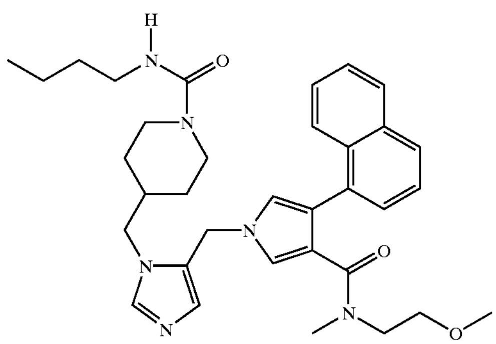 |
| 11 | 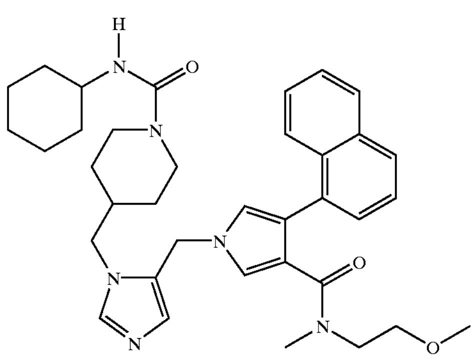 |

TABLE 1-2-continued

| COM. NO. | STRUCTURE |
|---|---|
| 12 | 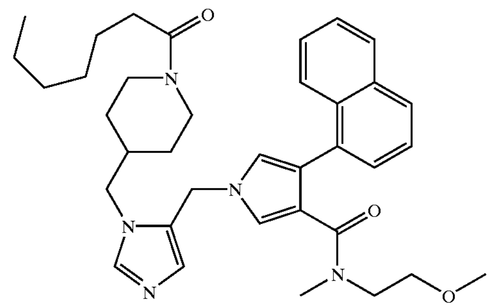 |
| 13 | 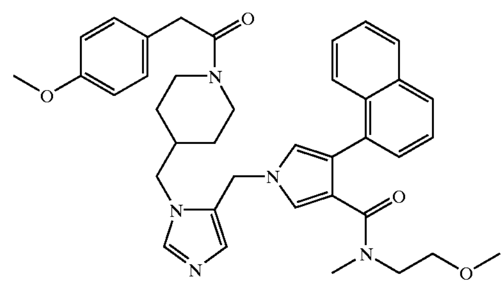 |
| 14 | 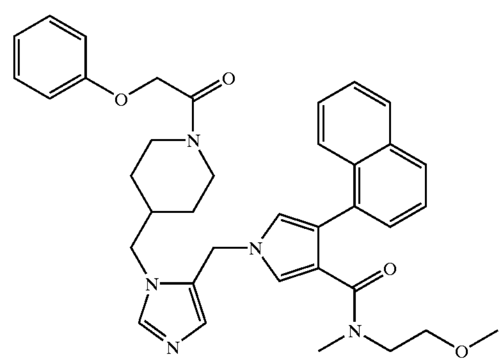 |
| 15 | 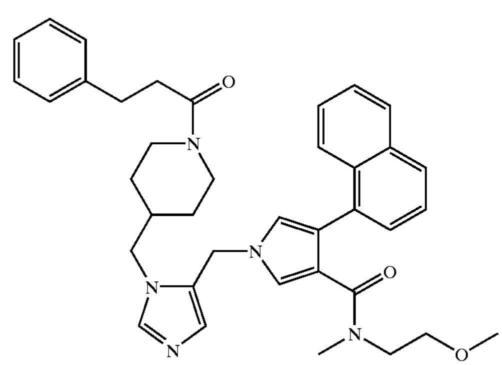 |

TABLE 1-2-continued
| COM. NO. | STRUCTURE |
|---|---|
| 16 | 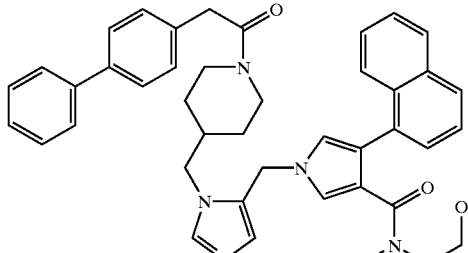 |
TABLE 1-3
| COM. NO. | STRUCTURE |
|---|---|
| 17 | 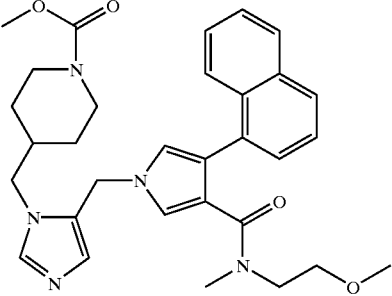 |
| 18 | 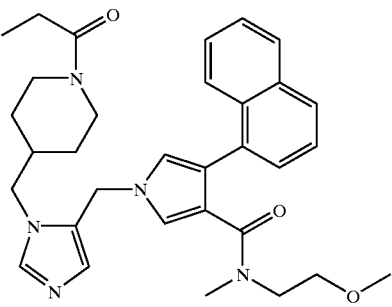 |
| 19 | 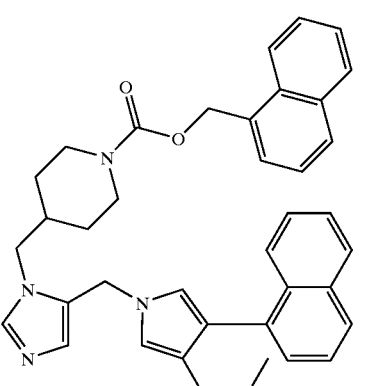 |
TABLE 1-3-continued
| COM. NO. | STRUCTURE |
|---|---|
| 20 | 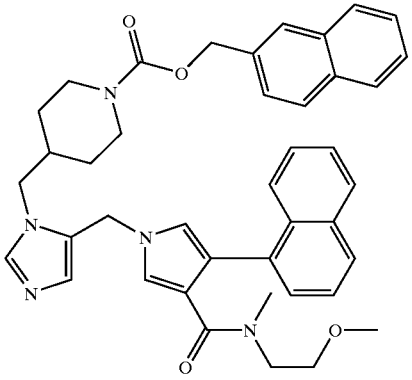 |
| 21 | 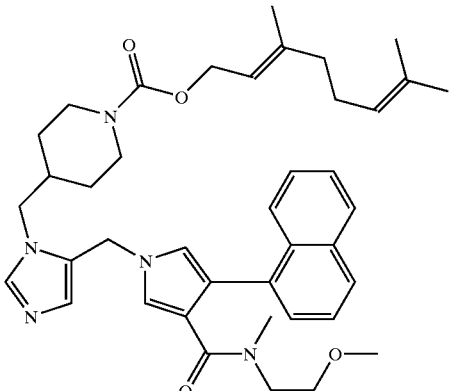 |
| 22 | 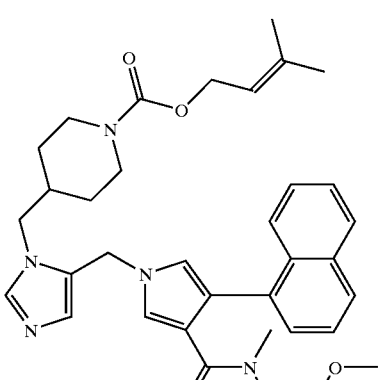 |

TABLE 1-4
| COM. NO. | STRUCTURE |
|---|---|
| 23 | 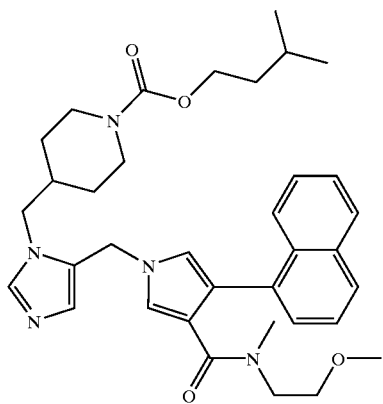 |
| 24 | 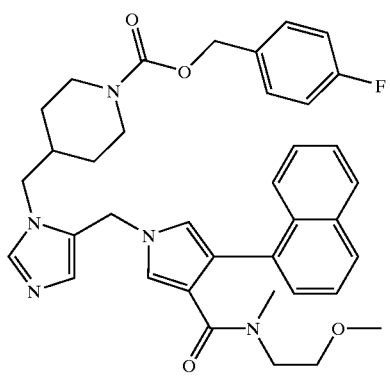 |
| 25 | 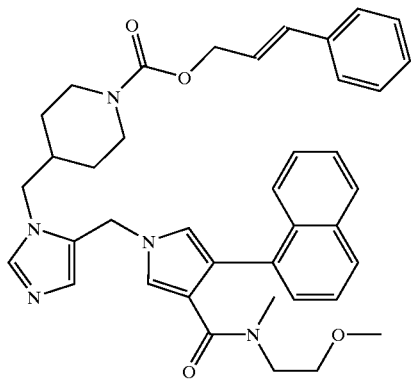 |
TABLE 1-4-continued
| COM. NO. | STRUCTURE |
|---|---|
| 26 | 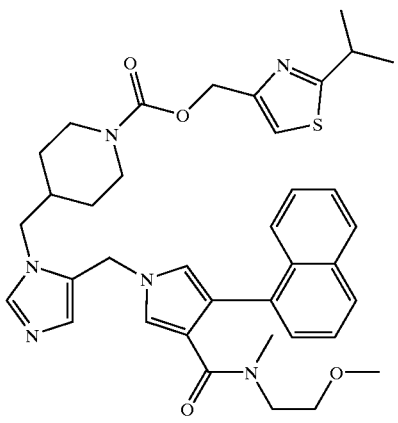 |
| 27 | 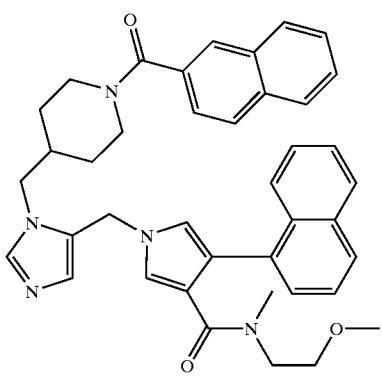 |
| 28 | 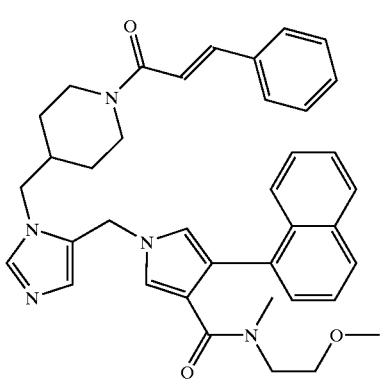 |

TABLE 1-5

| COM. NO. | STRUCTURE |
|---|---|
| 29 | 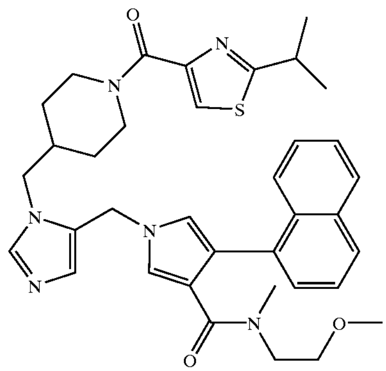 |
| 30 | 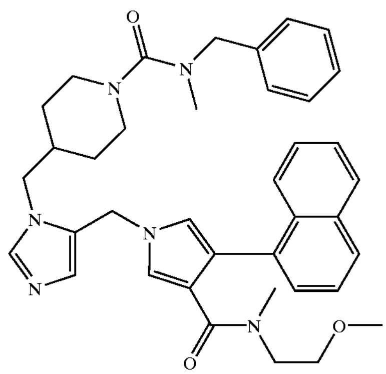 |
| 31 | 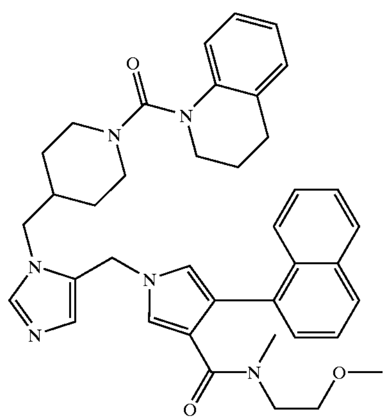 |
| 32 | 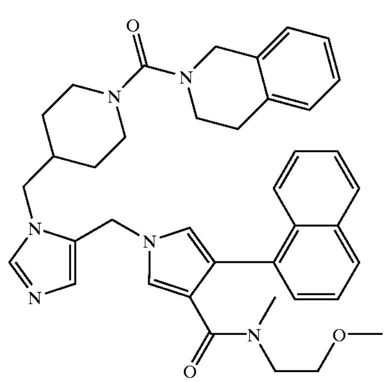 |

TABLE 1-5-continued

| COM. NO. | STRUCTURE |
|---|---|
| 33 | 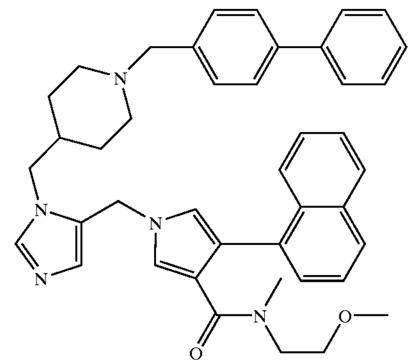 |
| 34 | 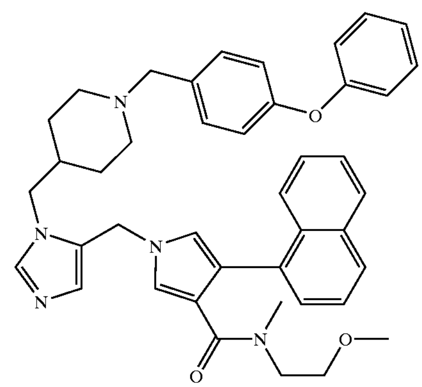 |

TABLE 1-6

| COM. NO. | STRUCTURE |
|---|---|
| 35 | 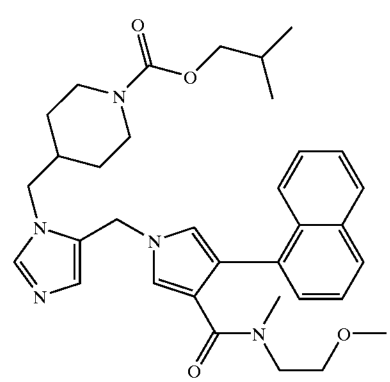 |

TABLE 1-6-continued
| COM. NO. | STRUCTURE |
|---|---|
| 36 | 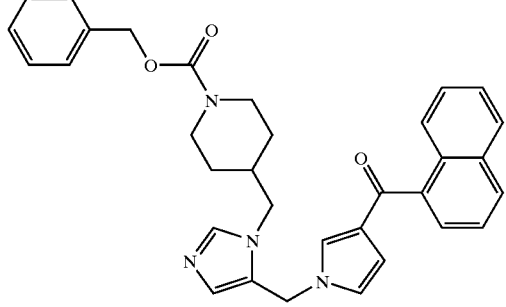 |
| 37 | 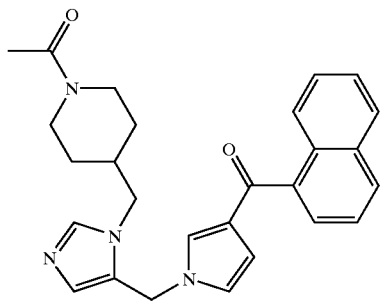 |
TABLE 1-7
| COM. NO. | STRUCTURE |
|---|---|
| 38 | 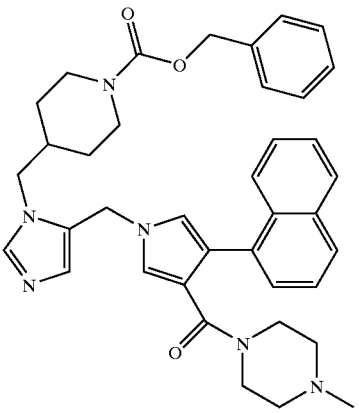 |
TABLE 1-7-continued
| COM. NO. | STRUCTURE |
|---|---|
| 39 | 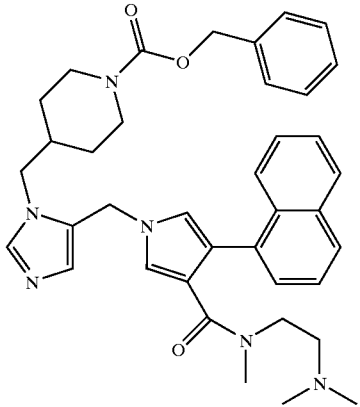 |
| 40 | 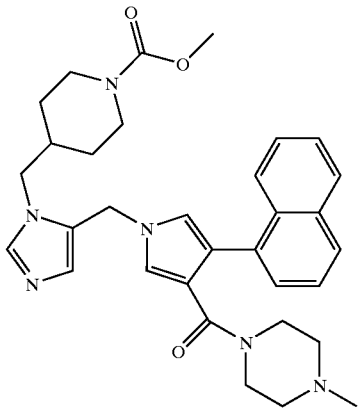 |
| 41 | 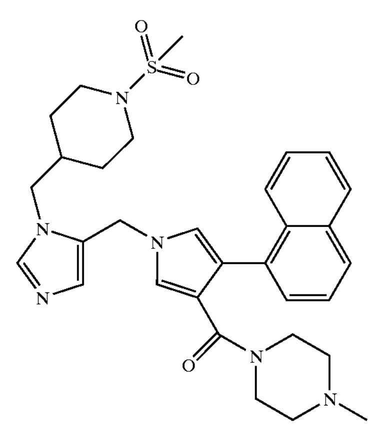 |

TABLE 1-7-continued

| COM. NO. | STRUCTURE |
|---|---|
| 42 | 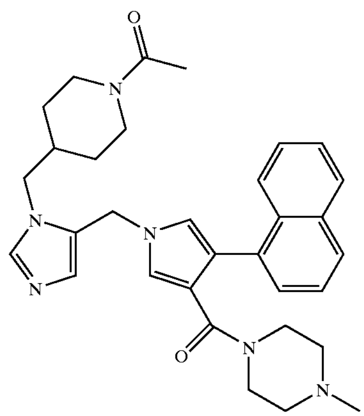 |
| 43 | 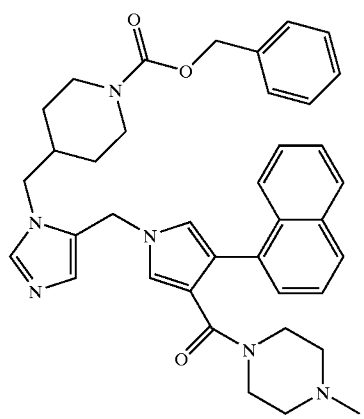 |

TABLE 1-8

| COM. NO. | STRUCTURE |
|---|---|
| 44 | 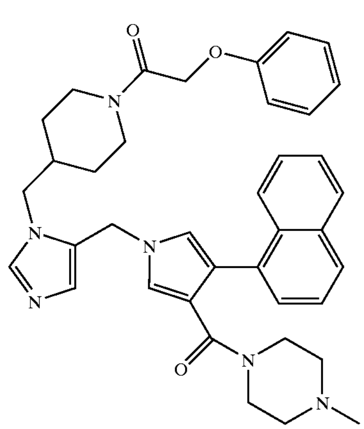 |

TABLE 1-8-continued

| COM. NO. | STRUCTURE |
|---|---|
| 45 | 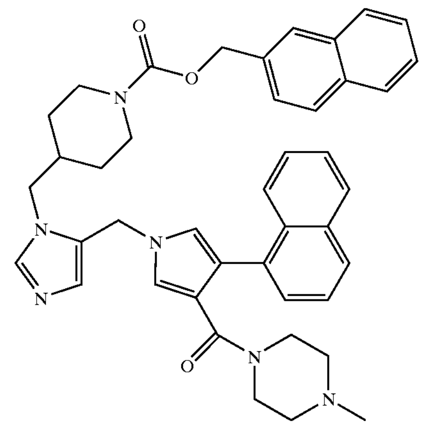 |
| 46 | 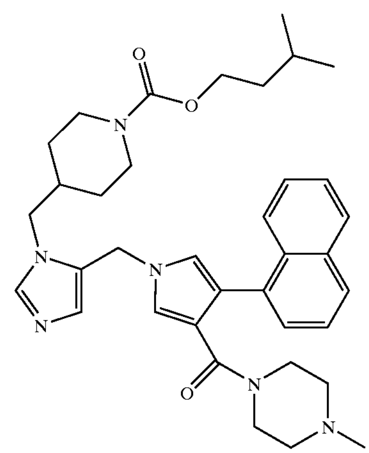 |
| 47 | 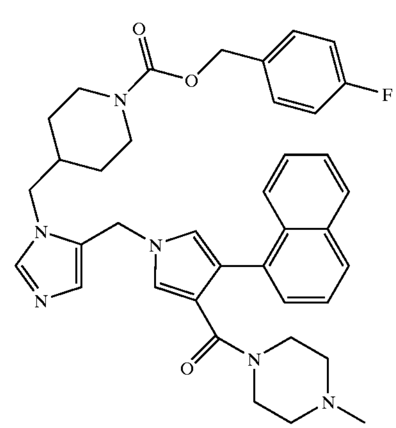 |

TABLE 1-8-continued
| COM. NO. | STRUCTURE |
|---|---|
| 48 | 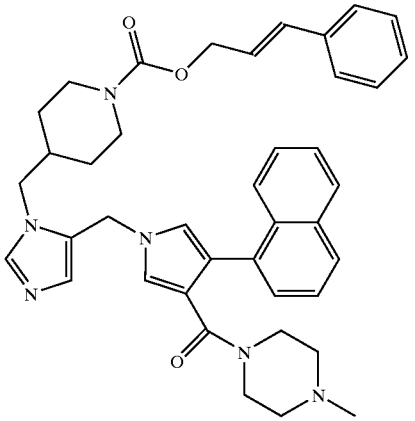 |
| 49 | 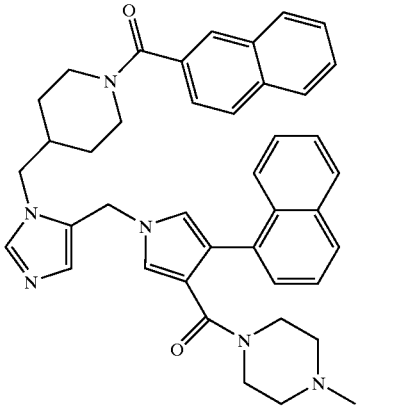 |
TABLE 1-9
| COM. NO. | STRUCTURE |
|---|---|
| 50 | 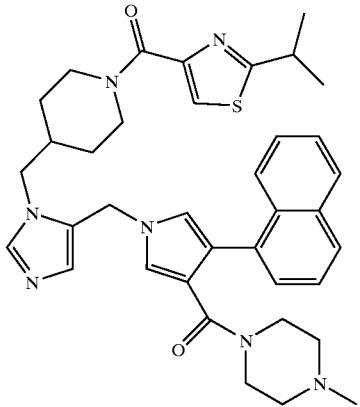 |
TABLE 1-9-continued
| COM. NO. | STRUCTURE |
|---|---|
| 51 | 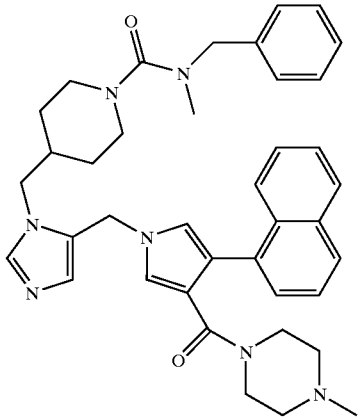 |
| 52 | 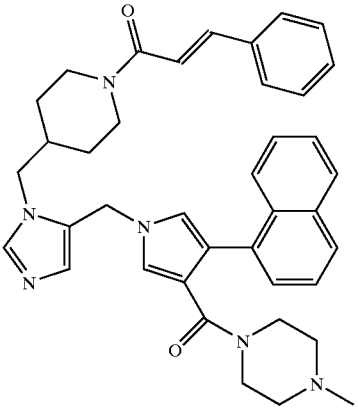 |
| 53 | 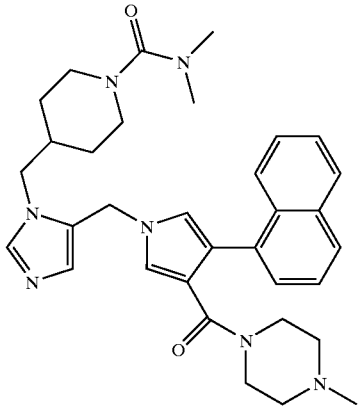 |

TABLE 1-9-continued

| COM. NO. | STRUCTURE |
|---|---|
| 54 | 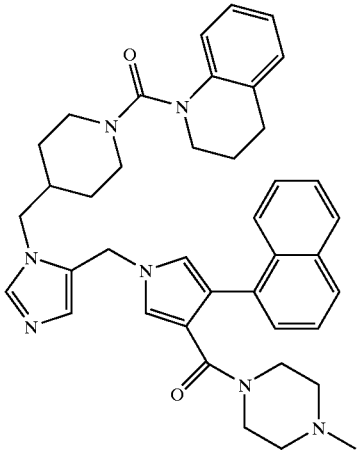 |
| 55 | 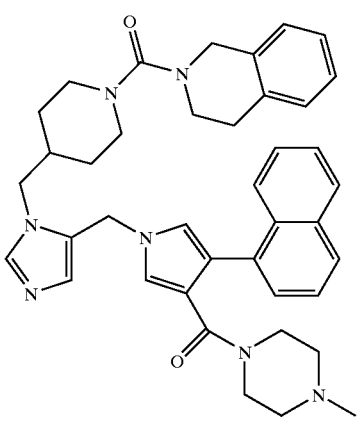 |

TABLE 1-10

| COM. NO. | STRUCTURE |
|---|---|
| 56 | 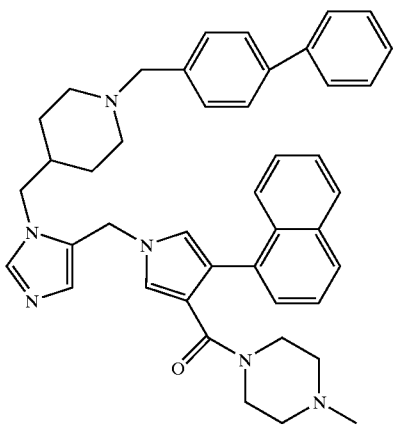 |

TABLE 1-10-continued

| COM. NO. | STRUCTURE |
|---|---|
| 57 | 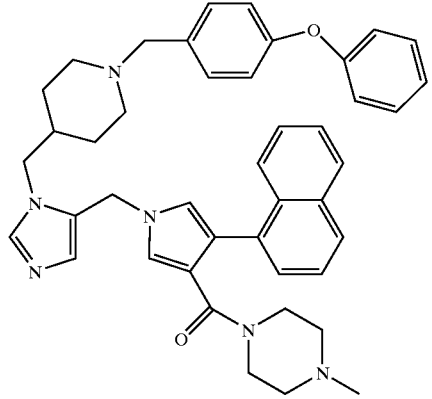 |

It is another object of the present invention to provide processes for preparing the piperidine derivative of formula (1) as defined above.

According to the present invention, the piperidine derivative of formula (1) can be prepared by a process characterized in that (a) a compound represented by the following formula (2a):

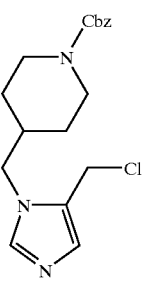

(2a)

wherein Cbz represents benzyloxycarbonyl and has the same meaning through the present specification, is reacted in a solvent in the presence of a base with a compound represented by the following formula (3):

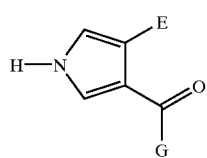

(3)

wherein E and G are defined as previously described, then the protecting group Cbz is eliminated to produce a compound represented by the following formula (1a):

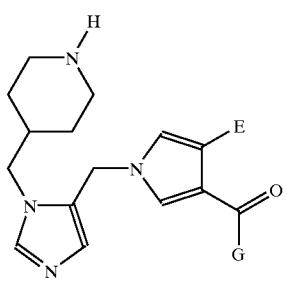
(1a)

wherein E and G are defined as previously described;

(b) the compound of formula (1a) is reacted in a solvent with a compound represented by the following formula (4):

A'—W  (4)

wherein A' is the same with A except that A' is not hydrogen, and W represents hydrogen, hydroxy or reactive leaving group, preferably halogen, to produce a compound represented by the following formula (1b):

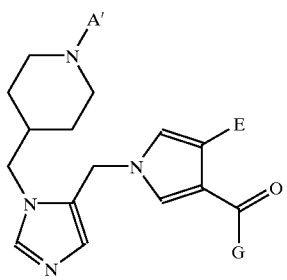
(1b)

wherein A', E and G are defined as previously described;

(c) the compound of formula (1a) is reacted in a solvent with a compound represented by the following formula (5):

A"—N=C=O  (5)

wherein A" represents lower alkyl, benzyl or $C_3$–$C_6$-cycloalkyl, to produce a compound represented by the following formula (1c):

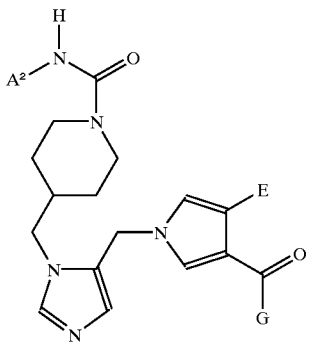
(1c)

wherein A", E and G are defined as previously described;

(d) the compound of formula (1a) is reacted in a solvent in the presence of a reducing agent with a compound represented by the following formula (6):

D—CHO  (6)

wherein D is defined as previously described, to produce a compound represented by the following formula (1d):

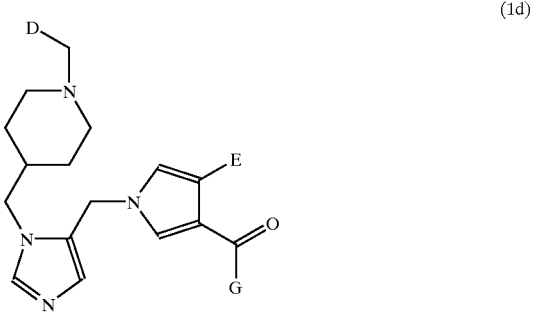
(1d)

wherein D, E and G are defined as previously described; or (e) the compound of formula (1a) is reacted in a solvent with phosgene and a compound represented by the following formula (7):

D'H  (7)

wherein D' represents a radical selected from the following group:

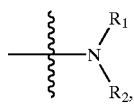

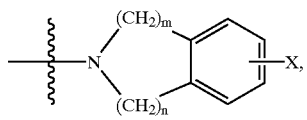

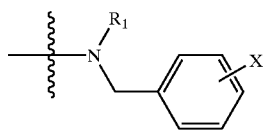

wherein m, n, X, $R_1$ and $R_2$ are defined as previously described, to produce a compound represented by the following formula (1e):

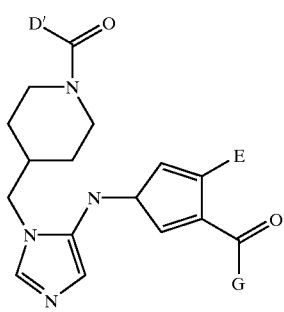

(1e)

wherein D', E and G are defined as previously described.

However, the compound according to the present invention may be conveniently prepared by any methods designed by combining various synthetic ways known in the prior arts, and such combination can be easily performed by a person having ordinary skill in this art. The process variants (a) to (e) will be more specifically explained below.

In process variants (a) to (e) for preparing the compound according to the present invention, any inert solvent which does not adversely affect to the reaction, preferably one or more selected from a group consisting of dimethylformamide, dichloromethane, tetrahydrofuran, chloroform and dimethylacetamide can be used. As the base in process variant (a), one or more selected from a group consisting of sodium hydride, potassium t-butoxide, sodium bis(trimethylsilyl)amide and potassium bis(trimethylsilyl)amide can be mentioned. Also, the deprotection reaction in process (a) to remove the benzyloxycarbonyl group at position-1 of piperidine ring may be carried out by applying the conventional reaction conditions, preferably by using $Pd(OH)_2/C$ or Pd/C in an alcohol solvent under hydrogen atmosphere.

In process variant (b), the compound of formula (1a) obtained in process variant (a) is coupled with the compound of formula (4) in the solvent as mentioned above optionally in the presence of a tertiary amine base to produce the compound of formula (1b). When the compound of formula (4) wherein W is hydroxy is used, the reaction is preferably carried out in the presence of a coupling agent. As the coupling agent, a mixture of 1-hydroxybenzotrizole(HOBT) and one or more substances selected from a group consisting of carbodiimides such as dicyclohexylcarbodiimide(DCC), 1-ethyl-3-(3-dimethylaminopropyl)carbodiimide(EDC), 1,1'-dicarbonyldiimidazole(CDI), etc. can be mentioned.

The compound of formula (1) wherein B is C=O, D is lower alkyl, benzyl or amino substituted by $C_3$–$C_6$-cycloalkyl[=compound of formula (1c)] may be prepared by reacting the compound of formula (1a) obtained in process variant (a) with the isocyanate derivative of formula (5).

In process variant (d), a reductive amination reaction is carried out in the presence of a reducing agent. As the reducing agent which can be used in this reaction, those conventionally recognized as a weak reducing agent such as Pd/C under hydrogen atmosphere, sodium triacetoxyborohydride or sodium cyanoborohydride can be mentioned.

On the other hand, a compound represented by the following formula (2) which includes the compound of formula (2a) used as a starting material in process variant (a) is a novel compound. Therefore, it is another object of the present invention to provide the compound of formula (2):

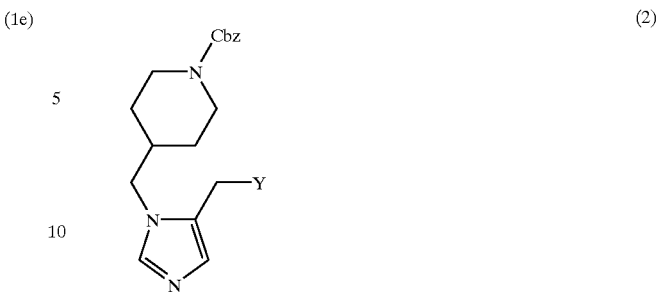

(2)

wherein Y represents hydroxy or chloro.

The novel intermediate of formula (2) can be prepared by processes characterized in that (f) a compound represented by the following formula (8):

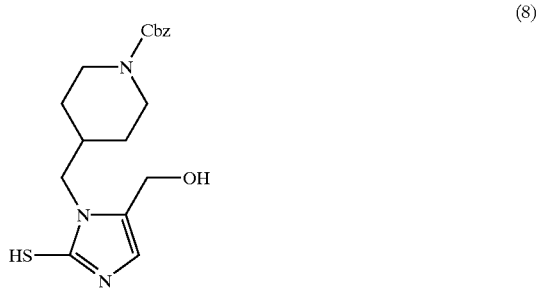

(8)

is desulfurated in an organic solvent in the presence of nitric acid to produce a compound represented by the following formula (2b):

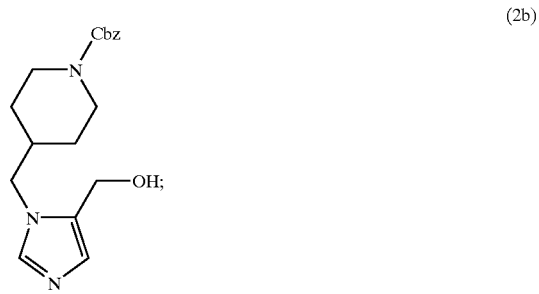

(2b)

or (g) the compound of formula (2b) is reacted with thionyl chloride($SOCl_2$) to produce the compound of formula (2a):

(2a)

In order to desulfurate the compound of formula (8), 10% nitric acid is used in the present invention. At this time, a small quantity of organic solvent should be added to the reaction solution because of the solubility problem of the bulky benzyloxycarbonylpiperidine group. Ethyl acetate or tetrahydrofuran can be used as the organic solvent. However, it is also possible to prepare the compound of formula (2b) from the compound of formula (8) using the other processes known as desulfuration conditions. In addition, the compound of formula (2b) thus obtained may be reacted with thionyl chloride to effectively prepare the compound of formula (2a).

As depicted in Reaction Scheme 1 below, the compound of formula (8) used as a starting material in preparing the compound of formula (2) may be synthesized from 4-(aminomethyl)piperidine by a process, in which protection, benzyloxycarbonylation and deprotection to an amine compound, and then reaction with dihydroxyacetone in the presence of KSCN are included. *J. Med. Chem.*, 33, 1312–1329, 1990 in which a similar reaction is explained in detail can be referred to for the specific reaction conditions.

Reaction Scheme 1

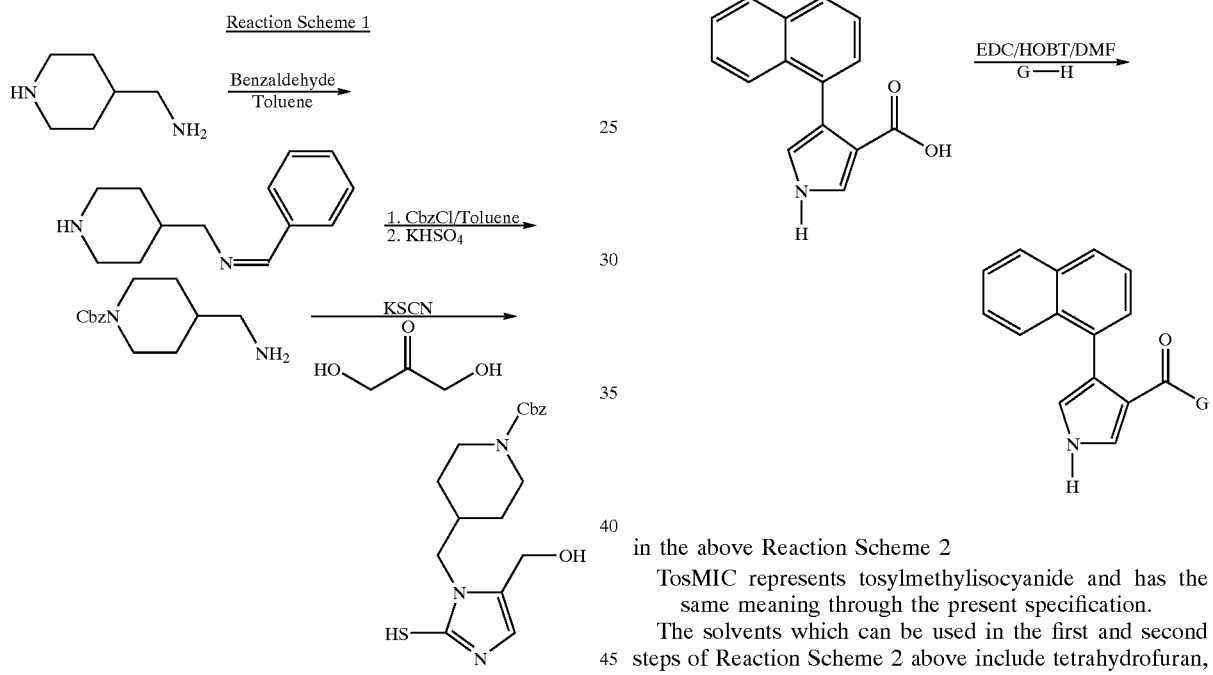

in the above Reaction Scheme 1

CbzCl represents benzylchloroformate and has the same meaning through the present specification.

The compound of formula (3) used as a reactant in preparing the compound of formula (1) may be synthesized from 1-naphthaldehyde or 1-naphthoic acid as depicted in Reaction Scheme 2 below.

Reaction Scheme 2

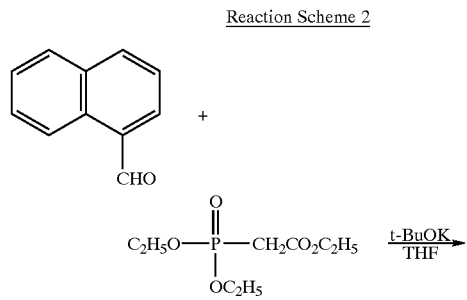

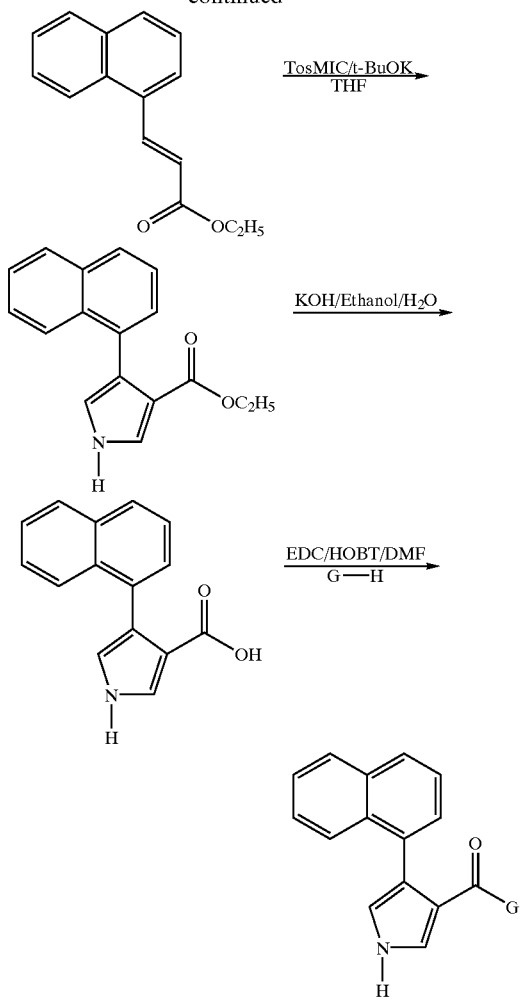

in the above Reaction Scheme 2

TosMIC represents tosylmethylisocyanide and has the same meaning through the present specification.

The solvents which can be used in the first and second steps of Reaction Scheme 2 above include tetrahydrofuran, acetonitrile and dimethylformamide. As the base, one or more selected from a group consisting of potassium t-butoxide, 1,8-diazabicyclo[5,4,0]undec-7-ene (DBU), potassium hydroxide and sodium hydroxide can be mentioned.

The reaction conditions including the amount of reactants, reaction temperature, reaction time, etc. in the processes according to the present invention can easily be determined by a person skilled in this art depending on the specific reactants.

In addition, the compound of formula (1) produced in the above processes in the form of a free base can easily be converted to a salt form as mentioned above according to the conventional methods known in this art.

After the reaction is completed, the resulting product may be further separated and/or purified by usual work-up processes, such as for example, chromatography, recrystallization, etc.

The compound of formula (1) prepared according to the processes above shows an inhibitory activity against farnesyl transferase, and thus can be effectively used as an anti-cancer agent. Therefore, the present invention also provides a pharmaceutical composition comprising the novel compound of formula (1), as defined above, or a pharmaceutically acceptable salt thereof as an active ingredient together with a pharmaceutically acceptable carrier. Particularly, the compound of formula (1) can be used very effectively for treating cancer, restenosis, atherosclerosis and infections from hepatitis delta and related viruses.

When the active compound according to the present invention is used for clinical purpose, it is preferably administered in an amount ranging from 5 to 200 mg per kg of body weight a day. The total daily dosage may be administered in one time or over several times. However, the specific administration dosage for the patient can be varied with the specific compound used, body weight of the subject patient, sex, hygienic condition, diet, time or method of administration, excretion rate, mixing ratio of the agent, severity of the disease to be treated, etc.

The compound of the present invention may be administered in the form of injections or oral preparations. Injections, for example, sterilized aqueous or oily suspension for injection, can be prepared according to the known procedure using suitable dispersing agent, wetting agent, or suspending agent. Solvents which can be used for preparing injections include water, Ringer's fluid and isotonic NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent and binding agent.

The present invention will be more specifically explained in the following examples. However, it should be understood that the following examples are intended to illustrate the present invention but not in any manner to limit the scope of the present invention. Processes for preparing the starting substances used for obtaining the compound of formula (1) will be also explained in detail in the following Preparations.

PREPARATION 1

Synthesis of 4-(5-Chloromethyl-1H-imidazol-1-ylmethyl)-piperidine-1-carboxylic Acid Benzylester 1-1) 4-Aminomethyl-piperidine-1-carboxylic Acid Benzylester 22.2 g(0.2 mol) of 4-aminomethyl-piperidine was dissolved in 250 ml of toluene and then 21.2 g(0.2 mol) of benzaldehyde was added thereto. The mixture was refluxed for 3 hours with Dean-stack and cooled down to 0° C., and then 34.2 g(0.2 mol) of benzylchloroformate was added dropwise thereto while stirring. After the mixture was stirred for 3 hours, 1N aqueous potassium hydrogen sulfate solution (220 ml) was added thereto at room temperature. The mixture was extracted three times with 200 mg of diethylether, and then the aqueous layer was basified with sodium hydroxide. The aqueous solution was saturated with sodium chloride and extracted three times with 100 ml of dichloromethane. The organic solution was dried over magnesium sulfate and distilled under reduced pressure to obtain 38 g(Yield 91%, Molecular weight 248) of the title compound.

$^1$H NMR(CDCl$_3$) δ 1.11(s, 2H), 1.49(s, 3H), 1.70(d, 2H), 2.57 (d, 2H), 2.78(s, 2H), 4.20(s, 2H), 5.12(s, 2H), 7.34–7.35(m, 5H); FAB(M+H): 249.

1-2) 4-(5-Hydroxymethyl-2-mercapto-1H-imidazol-1-ylmethyl)-piperidine-1-carboxylic Acid Benzylester 24.8 g(0.1 mol) of the compound prepared in Preparation 1-1) and 6.0 g(0.1 mol) of acetic acid were dissolved in 50 ml of isopropyl alcohol, and then the resulting solution was added to a solution wherein 12.6 g(0.13 mol) of potassium thiocyanate, 9.0 g(0.05 mol) of 1,3-dihydroxyacetone dimer and 10.0 g(0.17 mol) of acetic acid were dissolved in 50 ml of n-butanol. The whole mixture was stirred for 48 hours. The solvent was removed by distillation under reduced pressure, 200 ml of ethyl acetate was added to the residue, and the mixture was washed three times with 100 ml of water. The organic layer was dried over magnesium sulfate, and the solvent was removed by distillation under reduced pressure to obtain 27 g(75 mmol, Yield 75%, Molecular weight 361) of the title compound.

$^1$H NMR(CDCl$_3$) δ 1.22(d, 2H), 1.57(d, 2H), 2.30(s, 1H), 2.72 (s, 2H), 3,96(s, 2H), 4.15(d, 2H), 4.46(s, 2H), 5.10(s, 2H), 6.62(s, 1H), 7.26–7.37(m 5H); FAB(M+H): 362.

1-3) 4-(5-Hydroxymethyl-1H-imidazol-1-ylmethyl)-piperidine-1-carboxylic Acid Benzylester 18.05 g(50 mmol) of the compound prepared in Preparation 1-2) was added to a mixture of 100 ml of nitric acid(10%) and 10 ml of ethyl acetate. The whole mixture was cooled down using ice water, and stirred at room temperature for 3 hours. The mixture was basified with 4N aqueous sodium hydroxide solution, and then extracted twice with 100 ml of ethyl acetate. The organic extract was dried over magnesium sulfate and distilled under reduced pressure to obtain 12.3 g (38 mmol, Yield 75%, Molecular weight 329) of the title compound.

$^1$H NMR(CDCl$_3$) δ 1.16(d, 2H), 1.56(d, 2H), 1.98(s, 1H), 2.70 (s, 2H), 3,88(d, 2H), 4.18(s, 2H), 4.49(s, 1H), 4.52(br, 1H), 4.58(s, 2H), 5.10(s, 2H), 6.82(s, 1H), 7.27–7.40(m, 5H); FAB(M+H): 330.

1-4) 4-(5-Chloromethyl-1H-imidazol-1-ylmethyl)-piperidine-1-carboxylic Acid Benzylester 9.9 g(30 mmol) of the compound prepared in Preparation 1-3) was dissolved in 50 ml of chloroform, and 7.1 g(60 mmol) of thionyl chloride was slowly added dropwise thereto at 0° C. The mixture was stirred for 2 hours, the solvent was removed by distillation under reduced pressure, and the residual hydrochloric acid was removed under vacuum to obtain 9.9 g(Yield 95%, Molecular weight 347.5) of hydrochloride salt of the title compound.

$^1$H NMR(CDCl$_3$) δ 1.12(d, 2H), 1.53(d, 2H), 2.65(s, 2H), 3.82 (d, 2H), 4.22(s, 2H), 4.42(s, 1H), 4.49(s, 3H), 5.12(s, 2H), 6.60(s, 1H), 7.30–7.41(m, 5H); FAB(M+H): 349.

PREPARATION 2

Synthesis of 3-[N-(2-Methoxyethyl)-N-methyl]carbamoyl-4-(naphthalen-1-yl)-1H-pyrrole 2-1) 3-(Naphthalen-1-yl)-acrylic Acid Ethylester 22.4 g(0.10 mol) of triethylphosphonoacetate was dissolved in 500 ml of tetrahydrofuran and 12.4 g(1.1 mol) of potassium t-butoxide was slowly added thereto. To this solution was slowly added 15.6 g(0.10 mol) of 1-naphthaldehyde dissolved in 20 ml of tetrahydrofuran, then the resulting solution was stirred for 8 hours. The organic solvent was eliminated by distillation under reduced pressure, and the residue was dissolved in ethyl acetate, washed twice with water, dried over magnesium sulfate and concentrated. The concentrate was subjected to silica gel column chromatography(eluent: n-hexane/ethyl acetate=95/5, v/v) to obtain 20.3 g(0.090 mol, Yield 90%) of the title compound.

¹H NMR(CDCl₃) δ 1.33(t, 3H), 4.10(q, 2H), 6.75(q, 1H), 7.50(m, 3H), 7.73(d, 1H), 7.85(m, 2H), 8.10(d, 1H), 8.21(d, 1H); FAB 227 (M+H).

2-2) 3-(Ethoxycarbonyl)-4-(naphthalen-1-yl)-1H-pyrrole 5 g(18.9 mmol) of 3-(naphthalen-1-yl)-acrylic acid ethyl ester prepared in Preparation 2-1) and 3.68 g(18.9 mmol) of tosylmethylisocyanide were dissolved in 100 ml of tetrahydrofuran. To this solution was slowly added 2.55 g(22.7 mmol) of potassium t-butoxide dissolved in 100 ml of tetrahydrofuran, then the resulting solution was refluxed for 30 minutes. 100 ml of water was added to the reaction solution in order to stop the reaction, and the solvent was eliminated under reduced pressure. The residue was extracted with diethylether, washed with aqueous sodium chloride solution and dried over magnesium sulfate. The solvent was removed under reduced pressure and the residue was subjected to silica gel column chromatography(eluent: ethyl acetate/n-hexane=1/3, v/v) to obtain 3.85 g(14.5 mmol, Yield 77%) of the title compound.

¹H NMR(CDCl₃) δ 1.27(t, 3H), 4.07(q, 2H), 6.76(s, 1H), 7.28–7.47(m, 5H), 7.59(s, 1H), 7.82(m, 2H), 9.99(s, 1H); FAB 266 (M+H).

2-3) 3-Hydroxycarbonyl-4naphthalen-1-yl)-1H-pyrrole 2.64 g(10 mmol) of the compound prepared in Preparation 2-2) was dissolved in 50 ml of 50% ethanol, and 2.24 g(40 mmol) of potassium hydroxide was added thereto. The reaction solution was refluxed for 7 hours, cooled down to room temperature, adjusted to pH 4–5, extracted with ethyl acetate and dried over sodium sulfate. The solvent was removed under reduced pressure to obtain 1.62 g(8.1 mmol, Yield 81%) of the title compound. This compound was used in the next step reaction without purification.

¹H NMR(CDCl₃) δ 6.60(s, 1H), 7.32–7.49(m, 5H), 7.54 (s, 1H), 7.84(m, 2H), 9.92(s, 1H); FAB 238 (M+H).

2-4) 3-(Morpholin-4-yl)carbonyl-4-(naphthalen-1-yl)-1H-pyrrole 234 mg(1 mmol) of the compound prepared in Preparation 2-3) was dissolved in 2 ml of dimethylformamide, 230 mg(1.2 mmol) of EDC and 162 mg(1.7 mmol) of HOBT were added thereto, and the resulting mixture was stirred for 5 minutes at 0° C. 87 mg(1 mmol) of morpholine was added to the reaction solution, which was then stirred for 5 hours at room temperature. The solvent was removed under reduced pressure and 10 ml of saturated aqueous potassium carbonate solution was added to the residue. This solution was extracted with ethyl acetate, washed with 10 ml of 1N aqueous hydrochloric acid solution, washed with aqueous sodium chloride solution and water, dried over sodium sulfate and then concentrated to obtain 243 g(0.8 mmol, Yield 80%) of the title compound.

¹H NMR(CDCl₃) δ 2.13–3.52(br, 8H), 6.54(s, 1H), 7.31–7.51(m, 5H), 7.53 (s, 1H), 7.81(m, 2H), 9.93(s, 1H); FAB 307 (M+H).

2-5) 3-[N-(2-Methoxyethyl)-N-methyl]carbamoyl-4-(naphthalen-1-yl)-1H-pyrrole 234 mg(1 mmol) of the compound prepared in Preparation 2-3) was dissolved in 2 ml of dimethylformamide, 230 mg(1.2 mmol) of EDC, 101 mg (1 mmol) of triethylamine and 162 mg(1.7 mmol) of HOBT were added thereto, and the resulting mixture was stirred for 5 minutes at 0° C. 124 mg(1 mmol) of N-(2-methoxyethyl)-N-methylamine hydrochloride was added to the reaction solution, which was then stirred for 5 hours at room temperature. The solvent was removed under reduced pressure and 10 ml of saturated aqueous potassium carbonate solution was added to the residue. This solution was extracted with 20 ml of ethyl acetate, washed with 10 ml of 1N aqueous hydrochloric acid solution, washed with aqueous sodium chloride solution and water, dried over sodium sulfate and then concentrated to obtain 246 mg(0.8 mmol, Yield 80%) of the title compound.

¹H NMR(CDCl₃) δ 2.46(s, 2H), 2.80–3.40(m, 8H), 3,40 (s, 1H), 6.80(s, 1H), 7.00(s, 1H), 7.42(m, 4H), 7.73(d, 1H), 7.81(d, 1H), 8.17(d, 1H), 10.66 (s, 1H); FAB 309 (M+H).

PREPARATION 3

Synthesis of 4-Hydroxymethyl-2-(2-propyl)thiazole 3-1) 2-Methylpropionthioamide 3.0 g(43 mmol) of isobutyronitrile was dissolved in a solvent mixture of 30 ml of pyridine saturated with hydrogen sulfide gas and 9 ml of triethylamine, and the resulting solution was stirred for 12 hours at room temperature. The solvent was removed under reduced pressure and then the residue was dissolved in 200 ml of ethyl acetate and washed with 0.5N HCl and water. The organic layer was dried over anhydrous magnesium sulfate, concentrated and subjected to silica gel column chromatography(eluent: ethyl acetate/n-hexane=1/1, v/v) to obtain 3.1 g(30 mmol, Yield 70%) of the title compound.

¹H-NMR(CDCl₃) δ 1.26(d, 3H), 1.28(d, 3H), 2.92(m, 1H), 7.38(br, 1H), 8.32(br, 1H).

3-2) 4-Ethoxycarbonyl-2-(2-propyl)thiazole 3.0 g(29 mmol) of the compound prepared in Preparation 3-1) and 5.6 g(29 mmol) of ethyl bromopyruvate were dissolved in 50 ml of ethanol and the resulting mixture was refluxed for 3 hours. The solvent was removed under reduced pressure and the residue was subjected to column chromatography(eluent: ethyl acetate/n-hexane=1/4, v/v) to obtain 4.5 g(23 mmol, Yield 79%) of the title compound.

¹H-NMR(CDCl₃) δ 1.31–1.35(m, 9H), 3.34(m, 1H), 4.35 (q, 2H), 8.11(s, 1H).

3-3) 4-Hydroxymethyl-2-(2-propyl)thiazole 95 mg(2.5 mmol) of lithium aluminum hydride was added to 3 ml of tetrahydrofuran at 0° C. and 500 mg(2.51 mmol) of the compound prepared in Preparation 3-2) was slowly added thereto. The resulting mixture was stirred for 10 minutes at room temperature and 10 ml of water was carefully added thereto. This solution was extracted with ethyl acetate. The organic layer was dried over anhydrous magnesium sulfate and concentrated, and then the concentrate was subjected to column chromatography(eluent: ethyl acetate/n-hexane=7/3, v/v) to obtain 220 mg(1.40 mmol, Yield 56%) of the title compound.

¹H-NMR(CDCl₃) δ 1.34(d, 3H), 1.36(d, 3H), 3.27(m, 1H), 4.71(s, 2H), 5.22(s, 1H), 7.03(s, 1H).

PREPARATION 4

Synthesis of 2-(2-Propyl)thiazole-4-carboxylic Acid 200 mg(1.00 mmol) of the compound prepared in Preparation 3-2) was dissolved in a solvent mixture of tetrahydrofuran, methanol and water(1.0 ml/0.6 ml/0.3 ml) and 63 mg(1.5 mmol) of lithium hydroxide was added thereto. This reaction mixture was stirred for 1 hour at room temperature and the solvent was removed under reduced pressure. Water was added to the residue, which was then adjusted to about pH 6 using diluted aqueous hydrochloric acid solution and extracted with ethyl acetate. The organic layer was dried over anhydrous magnesium sulfate and concentrated to obtain 130 mg(1.40 mmol, Yield 76%) of the title compound. This compound was used in the next step reaction without further purification.

¹H-NMR(CDCl₃+CD₃OD) δ 1.25(m, 6H), 3.30(m, 1H), 8.05(s, 1H).

PREPARATION 5

Synthesis of 3-(Naphthalen-1-yl)carbonyl-1H-pyrrole 5-1) Methyl N-Methyl-1-naphthalene Hydroxamate 3.44 g(20 mmol) of 1-naphthoic acid was dissolved in 20 ml of dimethylformamide. To this solution were added 4.6 g(24 mmol) of EDC, 2.02 g(20 mmol) of triethylamine and 3.24 g(24 mmol) of HOBT, and the resulting mixture was stirred for 5 minutes at 0° C. 185 mg(20 mmol) of N,O-dimethylhydroxylamine hydrochloride was added thereto, and the mixture was stirred for 5 hours at room temperature. The solvent was removed under reduced pressure, 100 ml of saturated aqueous $K_2CO_3$ solution was added to the residue, which was then extracted with ethyl acetate. The organic layer was sequencially washed with 1N aqueous hydrochloric acid solution, aqueous sodium chloride solution and water, dried over anhydrous sodium sulfate and concentrated to obtain 3.04 g(1.50 mmol) of the title compound.

$^1$H NMR(CDCl$_3$) δ 2.42(s, 3H), 3.24(s, 3H), 7.47(m, 4H), 7.67(d, 1H), 7.74(m, 2H); FAB 216 (M+H).

5-2) 1-(Naphthalen-1-yl)-prop-2-en-1-one 2.03 g(9.4 mmol) of the compound prepared in Preparation 5-1) was dissolved in 20 ml of dry tetrahydrofuran, and 20 ml of 1N vinylmagnesiumbromide-tetrahydrofuran solution was slowly added thereto at 0° C. The mixture was stirred for 30 minutes at room temperature, 20 ml of 1N hydrochloric acid was added thereto, and the resulting mixture was extracted with 50 ml of ethyl acetate. The organic layer was dried over anhydrous magnesium sulfate, and the solvent therein was removed under reduced pressure to obtain 1.63 g(9 mmol, Yield 96%) of the title compound.

$^1$H NMR(CDCl$_3$) δ 6.92(m, 1H), 7.51(m, 4H), 7.74(d, 1H), 7.85(m, 2H), 7.98(d, 1H), 8.31(d, 1H).

5-3) 3-(Naphthalen-1-yl)carbonyl-1H-pyrrole 901 mg(5 mmol) of the compound prepared in Preparation 5-2) and 1.01 g(5.5 mmol) of tosylmethylisocyanide were dissolved in 10 ml of tetrahydrofuran, and then 555 mg(5.5 mmol) of potassium t-butoxide in tetrahydrofuran (10 ml) was slowly added thereto. The reaction solution was stirred for 30 minutes and 10 ml of water was added to the solution in order to stop the reaction. The solvent was removed under reduced pressure. 20 ml of water was added to the residue, which was then extracted with ethyl acetate, washed with aqueous sodium chloride solution and then dried over anhydrous magnesium sulfate. The solvent was removed under reduced pressure and the residue was subjected to column chromatography(eluent: ethyl acetate/n-hexane=1/3, v/v) to obtain 884 mg(4 mmol, Yield 80%) of the title compound.

$^1$H NMR(CDCl$_3$) δ 6.57(s, 1H), 6.66(s, 1H), 6.79(s, 1H), 7.36(m, 3H), 7.48(d, 1H), 7.77(d, 1H), 7.82(d, 1H), 8.04(d, 1H), 9.91(s, 1H).

EXAMPLE 1

Synthesis of 1-[1-(1-Benzyloxycarbonyl-piperidin-4-ylmethyl)-1H-imidazol-5-ylmethyl]-3-(morpholin-4-yl)carbonyl-4-(naphthalen-1-yl)-1H-pyrrole(1)

612 mg(2.0 mmol) of the compound prepared in Preparation 2-4) was dissolved in 10 ml of dimethylformamide, 264 mg(6.6 mmol) of sodium hydride(60%) was added thereto at 0° C., and then the resulting mixture was stirred for 5 minutes. To this mixture was added 765 mg (2.2 mmol) of the compound prepared in Preparation 1-4) and the whole mixture was stirred for 5 hours at room temperature. The solvent was removed by distillation under reduced pressure and 10 ml of water was added to the residue. The resulting mixture was extracted twice with 20 ml of ethyl acetate, dried over magnesium sulfate, concentrated and subjected to silica gel column chromatography(eluent: dichloromethane/methanol=90/10, v/v) to obtain 930 mg(Yield 75 %) of the title compound.

$^1$H NMR(CDCl$_3$) δ 1.11(d, 2H), 1.51(m, 3H), 2.30(br, 1H), 2.54–3.41(br, 9H), 3.75(d, 2H), 4.18(s, 2H), 5.10(s, 2H), 5.18(s, 2H), 6.75(s, 1H), 7.18(s, 1H), 7.20–7.53(m, 10H), 7.71(s, 1H), 7.82(d, 1H), 7.88(d, 1H), 8.07(d, 1H); FAB (M+H) 618.

EXAMPLE 2

Synthesis of 3-(Morpholin-4-yl)carbonyl-4-(naphthalen-1-yl)-1-[1-piperidin-4-ylmethyl)-1H-imidazol-5-ylmethyl]-1H-pyrrole(2)

227 mg(0.36 mmol) of the compound prepared in Example 1 was dissolved in 5 ml of methanol, 20 mg of palladium hydroxide carbon (Pd(OH)$_2$/C) was added thereto, and the mixture was reacted for 2 hours under 1 atm of hydrogen gas. The reactants were filtered and the solvent was removed. The residue was subjected to silica gel column chromatography(eluent: ammonia water/methanol=15/85, v/v) to obtain 120 mg(0.26 mmol Yield 74%) of the title compound.

$^1$H NMR(CD$_3$OD) δ 1.07(m, 2H), 1.25–1.48(m, 3H), 2.25(br, 3H), 2.40(m, 2H), 2.60–3.40(m, 8H), 3.78(d, 2H), 5.22(s, 2H), 6.88(s, 1H), 7.12(d, 2H), 7.26(m, 1H), 7.35 (m, 3H), 7.63(s, 1H), 7.75(d, 1H), 7.80(d, 1H), 7.93(d, 1H); FAB (M+H) 484.

EXAMPLE 3

Synthesis of 1-[1-(1-Acetylpiperidin-4-ylmethyl)-1H-imidazol-5-ylmethyl]-3-(morpholinyl)carbonyl-4-(naphthalen-1-yl)-1H-pyrrole(3)

30 mg(62 μmol) of the compound prepared in Example 2 was added to 2 ml of dichloromethane and then 5.4 mg(6.9 μmol) of acetyl chloride was added thereto using a syringe. The mixture was reacted for 2 hours. The solvent was removed under reduced pressure and the residue was subjected to silica gel column chromatography(eluent: dichloromethane/methanol=80/20, v/v) to obtain 26 mg(5.3 g mol, Yield 85%) of the title compound.

$^1$H NMR(CDCl$_3$+CD$_3$OD) δ 1.09–1.35(m, 3H), 1.45–1.75(m, 4H), 2.08(s, 3H), 2.10(br, 1H), 2.30(br, 1H), 2.44(t, 1H), 2.96(t, 2H), 3.08(br, 2H), 3.30(br, 1H), 3.79(d, 1H), 3.89(d, 2H), 4.55(d, 1H), 5.25(s, 2H), 6.80(s, 1H), 7.18(s, 1H), 7.28–7.52(m, 5H), 7.83(d, 1H), 7.99(d, 1H), 8.01(d, 1H), 8.06(s, 1H); FAB (M+H) 526.

EXAMPLE 4

Synthesis of 1-[1-(1-Methylsulfonyl-piperidin-4-ylmethyl)-1H-imidazol-5-ylmethyl]-3-(morpholin-4-yl)carbonyl-4-(naphthalen-1-yl)-1H-pyrrole(4)

30 mg(62 μmol) of the compound prepared in Example 2 was added to 2 ml of dichloromethane and then 7.8 mg(6.9 μmol) of methyl sulfonylchloride was added thereto using a syringe. The mixture was reacted for 2 hours. The solvent was removed under reduced pressure and the residue was subjected to silica gel column chromatography (eluent: dichloromethane/methanol=90/10, v/v) to obtain 25 mg(4.6 μmol, Yield 85%) of the title compound.

$^1$H NMR(CDCl$_3$+CD$_3$OD) δ 1.08(m, 2H), 1.35–1.65(m, 3H), 2.25(br, 2H), 2.45(t, 2H), 2.65(s, 3H), 2.75–3.40(br,

6H), 3.54(d, 2H), 3.82(d, 2H), 5.23(s, 2H), 6.91(s, 1H), 7.14(m, 2H), 7.26(d, 1H), 7.32–7.50(m, 3H), 7.68(s, 1H), 7.76(d, 1H), 7.82(d, 1H), 7.93(d, 1H); FAB (M+H) 562.

EXAMPLE 5

Synthesis of 1-[1-(1-Benzyloxycarbonyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(5)

616 mg(2.0 mmol) of title compound prepared in Preparation 2-5) was dissolved in 10 ml of dimethylformamide, 264 mg(6.6 mmol) of sodium hydride (60%) was added thereto at 0° C., and then the resulting mixture was stirred for 5 minutes. 765 mg(2.2 mmol) of the compound prepared in Preparation 1-4) was added to the mixture and the whole mixture was stirred for 5 hours at room temperature. The solvent was removed by distillation under reduced pressure and 10 ml of water was added to the residue. This solution was extracted twice with 20 ml of ethyl acetate, dried over magnesium sulfate, concentrated, and then subjected to silica gel column chromatography(eluent: dichloromethane/methanol=90/10, v/v) to obtain 930 mg(Yield 75 %) of the title compound.

$^1$H NMR(CDCl$_3$) δ 1.11(s, 2H), 1.35–1.65(m, 3H), 2.39 (s, 2H), 2.70(br, 4H), 2.90–3.20(m, 5H), 3.32(s, 1H), 3.78(d, 2H), 4.16(br, 2H), 5.08(s, 2H); 5.16 (s, 2H), 6.74(s, 1H), 7.10(s, 1H), 7.21–7.50(m, 10H), 7.76(d, 1H), 7.84(d, 1H), 7.91(s, 1H), 8.07(d, 1H); FAB (M+H) 620.

EXAMPLE 6

Synthesis of 3-[N-(2-Methoxyethyl)-N-methyl] carbamoyl-4-(naphthalen-1-yl)-1-[1-(piperidin-4-ylmethyl)-1H-imidazol-5-ylmethyl]-1H-pyrrole(6)

227 mg(0.36 mmol) of the compound prepared in Example 5 was dissolved in 5 ml of methanol. 20 mg of palladium hydroxide carbon was added thereto, and then the resulting mixture was reacted for 2 hours under 1 atm of hydrogen gas. The reactants were filtered, the solvent was removed, and then the residue was subjected to silica gel column chromatography(eluent: ammonia water/methanol= 15/85, v/v) to obtain 128 mg(0.26 mmol, Yield 74%) of the title compound.

$^1$H NMR(CDCl$_3$) δ 1.10–1.30(br, 3H), 1.47(d, 2H), 2.30–2.60(m, 4H), 2.68(br, 1H), 2.90–3.18(m, 6H), 3.29(s, 1H), 3.63(m, 2H), 4.04(br, 2H), 5.06(s, 2H), 6.71(s, 1H), 7.04(s, 1H), 7.12(s, 1H), 7.26–7.57(m, 5), 7.71(d, 1H), 7.79(d, 1H), 8.05(d, 1H); FAB (M+H) 486.

EXAMPLE 7

Synthesis of 1-[1-(1-Acetyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(7)

30 mg(62 μmol) of the compound prepared in Example 6 was added to 2 ml of dichloromethane, and 5.4 mg(6.9 μmol) of acetyl chloride was added thereto using a syringe. The resulting mixture was reacted for 2 hours, the solvent was removed under reduced pressure, and then the residue was subjected to silica gel column chromatography (eluent: dichloromethane/methanol=80/20, v/v) to obtain 27.8 mg(5.3 μmol, Yield 85%) of the title compound.

$^1$H NMR(CDCl$_3$) δ 1.05–1.35(br, 3H), 1.51(m, 3H), 2.04 (s, 3H), 2.41(br, 3H), 2.72(br, 1H), 2.88–3.22(m, 6H), 3.33 (br, 1H), 3.75(d, 1H), 4.01(d, 2H), 4.58(d, 1H), 5.28(s. 2H), 6.79(s, 1H), 7.18(s, 1H), 7.25–7.55(m, 5H), 7.78(d, 1H), 7.86(d, 1H), 8.09(d, 1H), 8.78(s, 1H); FAB (M+H) 528.

EXAMPLE 8

Synthesis of 3-[N-(2-Methoxyethyl)-N-methyl] carbamoyl-1-[1-(1-methylsulfonyl-piperidin-4-ylmethyl)-1H-imidazol-5-ylmethyl]-4-(naphthalen-1-yl)-1H-pyrrole(8)

30 mg(62 μmol) of the compound prepared in Example 6 was added to 2 ml of dichloromethane, and 7.8 mg(6.9 μmol) of methylsulfonyl chloride was added thereto using a syringe. The resulting mixture was reacted for 2 hours, the solvent was removed under reduced pressure, and then the residue was subjected to silica gel column chromatography (eluent: dichloromethane/methanol=90/10, v/v) to obtain 26 mg(4.6 μmol, Yield 85%) of the title compound.

$^1$H NMR(CDCl$_3$) δ 1.25(br, 4H), 1.55(br, 2H), 2.43(br, 4H), 2.70(s, 3H), 2.81–3.24(m, 6H), 3.34(br, 1H), 3.68(d, 2H), 4.04(d, 2H), 5.27(s, 2H), 6.80(s, 1H), 7.15(s, 1H), 7.25–7.55(m, 5H), 7.78(d, 1H), 7.87(d, 1H), 8.05(d, 1H), 8.64(s, 1H); FAB (M+H) 564.

EXAMPLE 9

Synthesis of 1-{1-[1-(N-Benzylcarbamoyl)-piperidin-4-ylmethyl]-1H-imidazol-5-ylmethyl}-3-[N-(2-methoxyethyl)-N-methyl]carbamoyl (naphthalen-1-yl)-1H-pyrrole(9)

62 mg(128 μmol) of the compound prepared in Example 6 was added to 2 ml of dichloromethane, and 20.5 mg(153 μmol) of benzyl isocyanate was added thereto. The resulting mixture was reacted for 3 hours, the solvent was removed, and then the residue was subjected to silica gel column chromatography(eluent: dichloromethane/methanol=95/5, v/v) to obtain 62 mg(Yield 78%) of the title compound.

$^1$H NMR(CDCl$_3$) δ 1.01(br, 2H), 1.30–1.51(m, 3H), 2.42 (s, 1H), 2.50–2.72 (m, 6H), 2.90–3.10 (m, 6H), 3.30(s, 1H), 3.42(s, 3H), 3.30(d, 1H), 4.92(d, 2H), 5.25(br, 1H), 6.72(s, 1H), 7.01(s, 1H), 7.15–7.30(m, 7H), 7.55(m, 3H), 7.60(s, 1H), 7.75(d, 1H), 7.85(d, 1H), 8.07(d, 1H); FAB (M+H) 619.

EXAMPLE 10

Synthesis of 1-{1-[1-(N-Butylcarbamoyl)-piperidin-4-ylmethyl]-1H-imidazol-5-ylmethyl}-3[N-(2-methoxyethyl)-N-methyl]carbamoyl-4-(naphthalen-1-yl)-1H-pyrrole(10)

62 mg(128 μmol) of the compound prepared in Example 6 was added to 2 ml of dichloromethane, and 15 mg(153 μmol) of butyl isocyanate was added thereto. The resulting mixture was reacted for 3 hours, the solvent was removed, and then the residue was subjected to silica gel column chromatography(eluent: dichloromethane/methanol=95/5, v/v) to obtain 61 mg(Yield 85%) of the title compound.

$^1$H NMR(CDCl$_3$) δ 0.91(t, 3H), 1.07(s, 2H), 1.57(m, 4H), 2.55(br, 2H), 2.61(br, 2H), 2.71–2.90(m, 1H), 3.0–3.25(m, 8H), 3.31(br, 1H), 3.40(m, 3H), 3.73(br, 2H), 3.95(m, 2H), 4.85(br, 1H), 5.15(s, 2H), 6.71(s, 1H), 7.11(s, 1H), 7.35(m, 5H), 7.74(d, 1H), 7.85(d, 1H), 7.91(s, 1H), 8.07(s, 1H); FAB (M+H) 585.

EXAMPLE 11

Synthesis of 1-{1-[1-(N-Cyclohexylcarbamoyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(11)

62 mg(128 μmol) of the compound prepared in Example 6 was added to 2 ml of dichloromethane, and 19 mg(153

μmol) of cyclohexyl isocyanate was added thereto. The resulting mixture was reacted for 3 hours, the solvent was removed, and then the residue was subjected to silica gel column chromatography(eluent: dichloromethane/methanol=95/5, v/v) to obtain 49 mg(Yield 65%) of the title compound.

$^1$H NMR(CDCl$_3$) δ 1.09(m, 5H), 1.35(m, 3H), 1.45(dd, 2H), 1.60(dd, 1H), 1.67(dd, 2H), 1.82(dd, 2H), 2.42(t, 2H), 2.50–2.80(m, 3H), 2.90–3.20(m, 3H), 3.37(br, 1H), 3.50(s, 3H), 3.61(m, 1H), 3.72(d, 2H), 3.90(dd, 2H), 4.51(br, 1H), 5.18(s, 2H), 6.72(s, 1H), 7.08(s, 1H), 7.22(s, 1H), 7.31(t, 1H), 7.55 (br, 3H), 7.61(s, 1H), 7.75(d, 1H), 7.86(d, 1H), 8.08(d, 1H); FAB (M+H) 611.

EXAMPLE 12

Synthesis of 1-[1-(1-Heptanoyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(12)

62 mg(128 μmol) of the compound prepared in Example 6 was dissolved in 2 ml of dichloromethane, and 19 mg(128 μmol) of heptanoyl chloride was added thereto. The resulting mixture was reacted for 3 hours, the solvent was removed, and then the residue was subjected to silica gel column chromatography(eluent: dichloromethane/methanol=95/5, v/v) to obtain 31 mg(Yield 40%) of the title compound.

$^1$H NMR(CDCl$_3$) δ 0.90(t, 5H), 1.04(m, 2H), 1.20–1.40 (br, 7H), 1.50–1.70 (br, 4H), 2.19(t, 2H), 2.30(t, 2H), 2.41 (br, 1H), 2.71(br, 1H), 2.75–3.10(m, 4H), 3.12(s, 1H), 3.35 (s, 1H), 3.70(s, 2H), 3.81(d, 1H), 4.60(d, 1H), 5.12(s, 2H), 6.75(s, 1H), 7.10(s, 1H), 7.21(s, 1H), 7.31(t, 1H), 7.40–7.50 (m, 3H), 7.61(s, 1H), 7.75(d, 1H), 7.85(d, 1H), 8.07 (d, 1H); FAB (M+H) 598.

EXAMPLE 13

Synthesis of 1-{1-[1-(4-Methoxybenzylcarbonyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(13)

62 mg(128 μmol) of the compound prepared in Example 6 was dissolved in 2 ml of dichloromethane, and 23 mg(128 μmol) of 4-methoxyphenylacetyl chloride was added thereto. The resulting mixture was reacted for 3 hours, the solvent was removed, and then the residue was subjected to silica gel column chromatography(eluent: dichloromethane/methanol=95/5, v/v) to obtain 50 mg(Yield 62%) of the title compound.

$^1$H NMR(CDCl$_3$) δ 0.78(m, 1H), 1.07(m, 1H), 1.30(br, 1H), 1.40(dd, 1H), 1.51(dd, 1H), 2.40(br, 3H), 2.72(br, 1H), 2.85(br, 1H), 2.85–3.10(m, 3H), 3.17(br, 1H), 3,31(br, 1H), 3.40–3.75(m, 5H), 3.75–3.90(m, 5H), 4.48(d, 1H), 5.09(s, 2H), 6.71(s, 1H), 6.81(m, 2H), 7.02–7.15(m, 3H), 7.21(br, 1H), 7.31 (br, 1H), 7.35–7.45(m, 3H), 7.56(s, 1H), 7.75(d, 1H), 7.85(d, 1H), 8.08(d, 1H); FAB (M+H) 634.

EXAMPLE 14

Synthesis of 3-[N-(2-Methoxyethyl)-N-methyl] carbamoyl-4-(naphthalen-1-yl)-1-[1-(1-phenoxyacetyl-piperidin-4-ylmethyl)-1H-imidazol-5-ylmethyl]-1H-pyrrole(14)

62 mg(128 μmol) of the compound prepared in Example 6 was dissolved in 2 ml of dichloromethane, and 23 mg(128 μmol) of phenoxyacetyl chloride was added thereto. The resulting mixture was reacted for 3 hours, the solvent was removed, and then the residue was subjected to silica gel column chromatography(eluent: dichloromethane/methanol=95/5, v/v) to obtain 50 mg(Yield 63%) of the title compound.

$^1$H NMR(CDCl$_3$) δ 1.10(m, 2H), 1.40(br, 1H), 1.57(m, 2H), 2.40(br, 3H), 2.70(br, 1H), 2.90–3.20(m, 7H), 3.31(br, 1H), 3.85(br, 2H), 3.98(d, 1H), 4.50 (d, 1H), 4.61(m, 2H), 5.21(s, 2H), 6.70(s, 1H), 6.87(d, 2H), 6.98(t, 1H), 7.17(s, 1H), 7.20–7.40(m, 4H), 7.40–7.50(m, 3H), 7.70(d, 1H), 7.73(d, 1H), 8.10(d, 1H), 8.14(s, 1H); FAB (M+H) 620.

EXAMPLE 15

Synthesis of 3-[N-(2-Methoxyethyl)-N-methyl] carbamoyl-4-(naphthalen-1-yl)-1-{1-[1-(2-phenylethylcarbonyl)-piperidin-4-ylmethyl]-1H-imidazol-5-ylmethyl}-1H-pyrrole(15)

62 mg(128 μmol) of the compound prepared in Example 6 was dissolved in 2 mg of dichloromethane, and 22 mg(128 μmol) of 3-phenylpropionyl chloride was added thereto. The resulting mixture was reacted for 3 hours, the solvent was removed, and then the residue was subjected to silica gel column chromatography(eluent: dichloromethane/methanol=95/5, v/v) to obtain 49 mg(Yield 63%) of the title compound.

$^1$H NMR(CDCl$_3$) δ 0.80(m, 1H), 1.01(m, 1H), 1.31(br, 1H), 1.42(d, 1H), 1.52(d, 1H), 2.35(m, 3H), 2.60(m, 2H), 2.51(t, 1H), 2.78(br, 1H), 2.80(m, 1H), 2.90–3.01(m, 4H), 3.01(s, 2H), 3.11(s, 1H), 3.31(br, 1H), 3.60–3.81(m, 3H), 4.61(d, 1H), 5.15(s, 2H), 6.75(s, 1H), 7.12(s, 1H), 7.15–7.35 (m, 7H), 7.45–7.50(m, 3H), 7.71(s, 1H), 7.79(d, 1H), 7.81(d, 1H), 8.08(d, 1H); FAB (M+H) 618.

EXAMPLE 16

Synthesis of 1-{1-[1-(4-Biphenylacetyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(16)

62 mg(128 μmol) of the compound prepared in Example 6 was dissolved in 2 ml of dimethylformamide, to which were added 27 mg(128 μmol) of 4-biphenylacetic acid, 14 mg(128 mmol) of 1-(3-dimethylaminopropyl)-3-ethylcarbodiimide hydrochloride and 17 mg(128 mmol) of N-hydroxybenzotriazole. The resulting mixture was reacted for 3 hours, the solvent was removed, and then 10 ml of ethyl acetate was added to the residue. The resulting solution was washed twice with 10 ml of water and furrier washed with 10 ml of 6N aqueous sodium hydrogen carbonate solution. The solvent was removed under reduced pressure and the residue was subjected to silica gel column chromatography (eluent: dichloromethane/methanol=95/5, v/v) to obtain 49 mg(Yield 62%) of the title compound.

$^1$H NMR(CDCl$_3$) δ 0.80(m, 1H), 1.10(m, 1H), 1.30(m, 1H), 1.42(d, 1H), 1.55(d, 1H), 2.35(m, 3H), 2.75(br, 1H), 2.85–3.24(m, 7H), 3.32(br, 1H), 3.60–3.80(m, 4H), 3.90(d, 1H), 4.61(d, 1H), 5.12(s, 2H), 6.72(s, 1H), 7.01(s, 1H), 7.20(s, 1H), 7.30(d, 2H), 7.32(t, 1H), 7.40–7.50(m, 5H), 7.50–7.60(m, 5H), 7.70(s, 1H), 7.72(d, 1H), 7.78(d, 1H), 8.09(d, 1H); FAB (M+H) 680.

EXAMPLE 17

Synthesis of 1-[1-(1-Methoxycarbonyl-piperidin-4-ylmethyl)-1H-imidazol-5-ylmethyl]-3[N-(2-methoxyethyl)-N-methyl]carbamoyl-4-(naphthalen-1-yl)-1H-pyrrole(17)

The title compound was obtained in a yield of 85% according to the same procedure as Example 7 except that methoxycarbonyl chloride was used instead of acetyl chloride.

¹H NMR(CDCl₃) δ 1.05(br, 2H), 1.32(br, 1H), 1.53(br, 2H), 2.31–2.72(m, 5H), 3.03~3.33(m, 7H), 3.62(s, 3H), 3.66(m, 2H), 4.13(br, 2H), 5.12(s, 2H), 6.71(s, 1H), 7.03(s, 1H), 7.14(s, 1H), 7.24–7.43(m, 5H), 7.74(d, 1H), 7.82 (d, 1H), 8.10(d, 1H); FAB (M+H) 544.

EXAMPLE 18

Synthesis of 3-[N-(2-Methoxyethyl)-N-methyl] carbamoyl-4-(naphthalen-1-yl)-1-[1-(1-propionyl-piperidin-4-ylmethyl)-1H-imidazol-5-ylmethyl]-1H-pyrrole(18)

The title compound was obtained in a yield of 82% according to the same procedure as Example 7 except that propionyl chloride was used instead of acetyl chloride.

¹H NMR(CDCl₃) δ 1.12(m, 5H), 1.40(m, 1H), 1.61(m, 2H), 2.35(q, 2H), 2.41(m, 3H), 2.70(br, 1H), 2.85(m, 1H), 3.02(m, 5H), 3.17(br, 1H), 3.31(br, 1H), 3.75(m, 3H), 4.55 (m, 1H), 5.17(s, 2H), 6.69(s, 1H), 7.09(s, 1H), 7.41 (m, 5H), 7.74(d, 1H), 7.83(d, 1H), 7.89(s, 1H), 8.05(d, 1H); FAB (M+H) 542.

EXAMPLE 19

Synthesis of 3-[N-(2-Methoxyethyl)-N-methyl] carbamoyl-4-(naphthalen-1-yl)-1-{1-[1-(1-naphthalen-1-ylmethyloxycarbonyl)piperidin-4-ylmethyl]-1H-imidazol-5-ylmethyl}-1H-pyrrole(19)

1.19 g(7.52 mmol) of 1-naphthalene-methanol was dissolved in 15 ml of toluene and 1.04 g(7.53 mmol) of potassium carbonate was added thereto. To this solution was added 3.89 ml(1.93M in toluene) of phosgene solution at 0° C., and the whole solution was stirred for 2 hours at room temperature. The reactants were filtered to remove solid materials and then 0.108 g(0.222 mmol) of the compound prepared in Example 6 and 0.046 ml(0.33 mmol) of triethylamine were added thereto. The resulting mixture was stirred for 1 hour at room temperature, and distilled under reduced pressure to remove the solvent. 10 ml of saturated aqueous sodium bicarbonate solution was added to the residue, which was then extracted with ethyl acetate, dried over anhydrous magnesium sulfate and concentrated. The concentrate was subjected to column chromatography (eluent: dichloromethane/methanol=95/5, v/v) to obtain 65 mg(0.097 mmol, Yield 44%) of the title compound.

¹H-NMR(CDCl₃) δ 1.10(br, 2H), 1.50(br, 2H), 2.36(s, 2H), 2.58–2.85(br, 4H), 2.90–3.23(br, 6H), 3.31(s, 1H), 3.70(s, 2H), 4.08(br, 1H), 4.25(br, 1H), 5.12(s, 2H), 5.51(s, 2H), 6.70(s, 1H), 7.04(s, 1H), 7.18(s, 1H), 7.29(m, 1H), 7.38–7.65(m, 7H), 7.70(s, 1H), 7.75(d, 1H), 7.79–7.95 (m, 3H), 8.00(d, 1H), 8.07(d, 1H); FAB (M+1) 670.

EXAMPLES 20 TO 26

The compounds physico-chemical data of which are represented in the following Table 2 were obtained according to the same procedure as Example 19.

TABLE 2-1

| COM. NO. | ¹H-NMR(CDCl₃) | FAB (M + 1) |
|---|---|---|
| 20 | 1.08(br, 2H), 1.61(br, 2H), 2.41(s, 2H), 2.71(br, 4H), 2.95–3.25(br, 6H), 3.30(br, 1H), 3.69(d, 2H), 4.15(br, 2H), 5.07(s, 2H), 5.24(s, 2H), 6.68(s, 1H), 7.08(s, 1H), 7.20(s, 1H), 7.31(m, 1H), 7.40–7.60(m, 6H), 7.66(s, 1H), 7.73–7.97(m, 6H), 8.12(d, 1H) | 670 |
| 21 | 1.15(m, 2H), 1.62(m, 10H), 2.10(m, 5H), 2L42(s, 2H), 2.71(br, 4H), 3.04(s, 4H), 3.14(s, 2H), 3.35(s, 1H), 3.76(d, 2H), 4.17(br, 2H), 4.59(s, 2H), 5.10(m, 1H), 5.19(s, 2H), 5.32(m, 1H), 7.10(s, 1H), 7.23(s, 1H), 7.36(m, 1H), 7.42(m, 3H), 7.75(s, 1H), 7.80(m 2H), 7.86(d, 1H), 8.10(d, 1H) | 666 |
| 22 | 1.04(m, 2H), 1.30–1.60(m, 4H), 1.64(s, 3H), 1.70(s, 3H), 2.38(br, 2H), 2.58(br, 2H), 2.67(br, 1H), 2.99(s, 3H), 3.08(br, 2H), 3.29(br, 1H), 3.66(d, 2H), 4.07(br, 2H), 4.50(d, 2H), 5.08(s, 2H), 5.20–5.30 (m, 1H), 6.69(s, 1H), 7.03(s, 1H), 7.15(s, 1H), 7.29–7.55(m, 5H), 7.52(d, 1H), 7.80(d, 1H), 8.04(d, 1H) | 598 |
| 23 | 0.89(d, 6H), 1.06(d, 2H), 1.35–1.80(m, 6H), 2.39(br, 2H), 2.50–2.89(br, 3H), 2.90–3.20(br, 5H), 3.31(br, 1H), 3.71(d, 2H), 3.90(br, 1H), 4.00–4.25 (m, 4H), 5.12(s, 2H), 6.71(s, 1H), 7.08(s, 1H), 7.20(s, 1H), 7.38(d, 1H), 7.40(m, 3H), 7.73(s, 1H), 7.75(d, 1H), 7.80(d, 1H), 8.05(d, 1H) | 600 |
| 24 | 1.38(br, 6H), 2.64(br, 9H), 3.68(br, 2H), 3.74(d, 2H), 4.12 (br, 2H), 5.02(s, 2H), 5.13(s, 2H), 6.72(s, 1H), 7.01(m, 4H), 7.39(m, 6H), 7.74(m, 2H), 7.83(d, 1H), 8.05(d, 1H) | 638 |

TABLE 2-2

| COM. NO. | ¹H-NMR(CDCl₃) | FAB (M + 1) |
|---|---|---|
| 25 | 1.11(br, 3H), 1.51(d, 2H), 3.01(br, 12H), 3.74(d, 2H), 4.14(s, 2H), 4.68(s, 2H), 5.13(s, 2H), 6.25(m, 1H), 6.56(d, 1H), 6.73(s, 1H), 7.08(s, 1H), 7.15–7.65 (m, 10H), 7.73(d, 1H), 7.77(s, 1H), 7.82(d, 1H), 8.06(d, 1H) | 646 |
| 26 | 1.24(m, 2H), 1.33(m, 6H), 1.38(m, 2H), 1.53(m, 2H), 2.41(m, 2H), 2.76(m, 2H), 3.01–3.32(m, 8H), 3.43(m, 2H), 3.69(m, 2H), 4.15(m, 2H), 5.11(s, 2H), 6.73(s, 1H), 7.06(s, 1H), 7.19(s, 1H), 7.25–7.45 (m, 5H), 7.65(s, 1H), 7.77(d, 1H), 7.83(d, 1H), 8.09(d, 1H) | 669 |

EXAMPLE 27

Synthesis of 3-[N-(2-Methoxyethyl)-N-methyl] carbamoyl-4-(naphthalen-1-yl)-1-{1-[1-(naphthalen-2-ylcarbonyl)piperidin-4-ylmethyl]-1H-imidazol-5-ylmethyl}-1H-pyrrole(27)

100 mg(0.206 mmol) of the compound prepared in Example 6 and 39 mg(0.22 mmol) of 2-naphthoic acid were dissolved in 1 ml of dimethylformamide, 59 mg(0.31 mmol) of EDC and 42 mg(0.31 mmol) of HOBT were added thereto, and then the mixture was stirred for 2 hours at room temperature. The solvent was removed by distillation under reduced pressure. The residue was dissolved in ethyl acetate and washed with saturated aqueous sodium bicarbonate solution. The organic layer was dried over anhydrous magnesium sulfate, concentrated, and subjected to column chromatography(eluent: dichloromethane/methanol=95/5, v/v) to obtain 83 mg(0.13 mmol, Yield 63%) of the title compound.

¹H-NMR(CDCl₃) δ 1.16(br, 2H), 1.60(br, 2H), 2.40(br, 2H), 2.60–3.23(m, 9H), 3.31(br, 1H), 3.71(s, 3H), 4.45(br, 1H), 4.70(br, 1H), 5.10(s, 2H), 6.72(d, 1H), 7.04(s, 1H), 7.17(s, 1H), 7.31(d, 1H), 7.35–7.55(m, 6H), 7.58(s, 1H), 7.73(d, 1H), 7.75–7.95(m, 5H), 8.04(d, 1H); FAB (M+1) 640.

EXAMPLES 28 TO 29

The compounds physico-chemical data of which are represented in the following Table 3 were obtained according to the same procedure as Example 27 except that trans-cinnamic acid and 2-(2-propyl)thiazole-4-carboxylic acid, respectively, were used instead of 2-naphthoic acid.

TABLE 3

| COM. NO. | $^1$H-NMR(CDCl$_3$) | FAB (M + 1) |
|---|---|---|
| 28 | 1.06(s, 2H), 1.37(s, 1H), 1.55(d, 2H), 2.25–2.60 (br, 4H), 2.70(br, 1H), 2.90–3.2(br, 6H), 3.30(br, 1H), 3.68(s, 2H), 4.06(m, 1H), 4.65(s, 1H), 5.10(s, 2H), 6.73(s, 1H), 6.83 (d, 1H), 7.04(s, 1H), 7.17(s, 1H), 7.25–7.52(m, 9H), 7.56(s, 2H), 7.71(d, 1H), 7.80(d, 1H), 8.07(d, 1H) | 616 |
| 29 | 1.22(m, 2H), 1.34(d, 3H), 1.36(d, 3H), 1.38(m, 2H), 1.47(m, 2H), 2.38(m, 2H), 2.52(m, 2H), 3.00–3.14 (m, 6H), 3.25(m, 2H), 3.68(m, 2H), 4.43(m, 1H), 4.62(m, 1H), 5.09(s, 2H), 6.72(s, 1H), 7.04(s, 1H), 7.16(s, 1H), 7.37–7.44(m, 5H), 7.65(s, 1H), 7.72(d, 1H), 7.81(d, 1H), 8.07(d, 1H) | 639 |

EXAMPLE 30

Synthesis of 1-{1-[1-(N-Benzyl-N-methylcarbamoyl)piperidin-4-ylmethyl]-1H-imidazol-5-ylmethyl}-3-[N-(2-methoxyethyl)-N-methyl]carbamoyl-4naphthalen-1-yl)1H-pyrrole(30)

100 mg(0.206 mmol) of the compound prepared in Example 6 was dissolved in 1 ml of tetrahydrofuran, and 27 mg(0.23 mmol) of N-benzyl-N-methylamine was added thereto. Then, 0.16 ml(1.93M in toluene) of phosgene solution was added dropwise thereto at 0° C. The resulting mixture was stirred for 1 hour at room temperature, 1 ml of water was added thereto, and then this solution was extracted with ethyl acetate. The organic layer was dried over anhydrous magnesium sulfate, concentrated, and subjected to column chromatography (eluent: dichloromethane/methanol=93/7, v/v) to obtain 81 mg(0.128 mmol, Yield 62%) of the title compound.

$^1$H-NMR(CDCl$_3$) δ 1.20(m, 2H), 1.49(d, 2H), 2.40(br, 2H), 2.56–2.85(m, 8H), 2.93–3.20(m, 5H), 3.29(br, 1H), 3.52(m, 4H), 3.65(d, 2H), 3.73(m, 2H), 4.3 1(s, 2H), 5.14(s, 2H), 6.71(d, 1H), 7.07(s, 1H), 7.29(m, 10H), 7.73(d, 1H), 7.75 (s, 1H), 7.82(d, 1H), 8.05(d, 1H); FAB (M+1) 633.

EXAMPLE 31

Synthesis of 3-[N-(2-Methoxyethyl)-N-methyl]carbamoyl-4-(naphthalen-1-yl)-1-{1-[1-(1,2,3,4-tetrahydroquinolin-1-ylcarbonyl)piperidin-4-ylmethyl]-1H-imidazol-5-ylmethyl}-1H-pyrrole(31)

The title compound was obtained according to the same procedure as Example 30 except that 1,2,3,4-tetrahydroquinoline was used instead of N-benzyl-N-methylamine.

EXAMPLE 32

Synthesis of 3-[N-(2-Methoxyethyl)N-methyl]carbamoyl-4-(naphthalen-1-yl)-1-{1-[1-(1,2,3,4-tetrahydroisoquinolin-2-ylcarbonyl)piperidin-4-ylmethyl]-1H-imidazol-5-ylmethyl}-1H-pyrrole(32)

The title compound was obtained according to the same procedure as Example 30 except that 1,2,3,4-tetrahydroisoquinoline was used instead of N-benzyl-N-methylamine.

EXAMPLE 33

Synthesis of 1-{1-[1-(4-Biphenylmethyl)piperidin-4-ylmethyl]-1H-imidazol-5-ylmethyl}-3-[N-(2-methoxyethyl)-N-methyl]carbamoyl-4-(naphthalen-1-yl-1H-pyrrole(33)

100 mg(0.206 mmol) of the compound prepared in Example 6 was dissolved in 3 ml of tetrahydrofuran, 45 mg(0.24 mmol) of 4-phenylbenzaldehyde and 52 mg(0.24 mmol) of sodium triacetoxyborohydride were added thereto, and the the resulting mixture was stirred for 10 hours at room temperature. 1 ml of 1N HCl-methanol solution was added to the reaction solution, which was then stirred for 30 minutes, basified and extracted with ethyl acetate. The organic layer was dried over anhydrous magnesium sulfate, concentrated and subjected to column chromatography (eluent: dichloromethane/methanol=93/7, v/v) to obtain 100 mg(0.154 mmol, Yield 75%) of the title compound.

EXAMPLE 34

Synthesis of 3-[N-(2-Methoxyethyl)-N-methyl]carbamoyl-4-(naphthalen-1-yl)-1-{1-[1-(4-phenoxybenzyl)piperidin-4-ylmethyl]-1H-imidazol-5-ylmethyl}-1H-pyrrole(34)

The title compound was obtained according to the same procedure as Example 33 except that 4-phenoxybenzaldehyde was used instead of 4-phenylbenzaldehyde.

Physico-chemical data of the compounds prepared in Examples 31 to 34 are represented in the following Table 4.

TABLE 4

| COM. NO. | $^1$H–NMR(CDCl$_3$) | FAB MS (M + 1) |
|---|---|---|
| 31 | 1.12(m. 2H), 1.43(d, 2H), 1.89(m, 2H), 2.39(s, 2H), 2.57(t, 2H), 2.70(m, 3H), 2.90–3.20(br, 7H), 3.30(s, 1H), 3.52(m, 2H), 3.69(d, 2H), 3.75(d, 2H), 5.10(s, 2H), 6.69(d, 1H), 6.84(m, 2H), 7.04(m, 3H), 7.16(s, 1H), 7.31(m, 1H), 7.37(m, 3H), 7.61(s, 1H), 7.74(d, 1H), 7.81(d, 1H), 8.04(d 1H) | 645 |
| 32 | 1.12(m, 2H), 1.43(d, 2H), 1.89(m, 2H), 2.39(s, 2H), 2.75(t, 2H), 2.85–3.15(br, 5H), 3.41(br, 2H), 3.52(br, 4H), 3.69(d, 2H), 3.75(d, 2H), 4.37(s, 2H), 5.11(s, 2H), 6.74(s, 1H), 7.00–7.70(m, 11H), 7.79(d, 1H), 7.84(d, 1H), 8.06(d, 1H) | 645 |
| 33 | 1.31(m, 3H), 1.50(m, 2H), 1.70(m, 4H), 1.91(m, 1H), 2.05(s, 1H), 2.41(s, 2H), 2.75(m, 1H), 2.90(m, 1H), 3.01(br, 2H), 3.09(m, 1H), 3.31(m, 1H), 3.51(s, 2H), 3.71(s, 2H), 5.12(s, 2H), 6.72(s, 1H), 7.10(s, 1H), 7.17(s, 1H), 7.20–7.70(m, 14H), 7.79(d, H), 7.84(d, 1H), 8.07(d, 1H) | 652 |
| 34 | 1.31(m, 2H), 1.51(m, 2H), 1.90(m, 4H), 1.91(m, 1H), 2.05(s, 1H), 2.42(s, 2H), 2.75(m, 1H), 2.87(m, 2H), 3.01(br, 2H), 3.09(m, H), 3.31(m, 1H), 3.51(s, 2H), 3.71(s, 2H), 5.13(s, 2H), 6.72(s, 1H), 6.95–7.70(m, 16H), 7.79(d, 1H), 7.84(d, 1H), 8.07(d, 1H) | 668 |

EXAMPLE 35

Synthesis of 1-[1-(1-Isobutoxycarbonyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(35)

The title compound was obtained in a yield of 80% according to the same procedure as Example 7 except that isobutylchloroformate was used instead of acetyl chloride.

1H-NMR(CDCl$_3$) δ 0.86(d, 6H), 1.04(m, 2H), 1.31(br, 1H), 1.47(m, 2H), 1.86(m, 1H), 2.38(br, 2H), 2.61(m, 3H), 2.99(br, 3H), 3.07(br, 2H), 3.29(br, 1H), 3.42(br, 1H), 3.66 (d, 2H), 3.77(d, 2H), 4.08(br, 2H), 5.08(s, 2H), 6.69(s, 1H), 7.03(s, 1H), 7.14(s, 1H), 7.32(m, 1H), 7.37(m, 3H), 7.52(s, 1H), 7.72(d, 1H), 7.80(d, 1H), 8.03(d, 1H); FAB (M+1) 586.

EXAMPLE 36

Synthesis of 1-{1-[1-(Benzyloxycarbonyl)piperidin-4-yl]methyl-1H-imidazol-5-yl}methyl-3-(naphthalen-1-yl)carbonyl-1H-pyrrole(36)

62.6 mg(0.28 mmol) of the compound prepared in Preparation 5-3) was dissolved in 1 ml of dimethylformamide, and 60 mg(1.5 mmol) of sodium hydride was added thereto. The mixture was stirred for 30 minutes at room temperature, 115 mg(0.30 mmol) of the compound prepared in Preparation 1-4) was added thereto, and then the resulting mixture was stirred for 1 hour. The solvent was removed under reduced pressure and 5 ml of saturated aqueous sodium bicarbonate solution was added to the residue. This solution was extracted with 20 ml of ethyl acetate. The organic layer was washed with aqueous sodium chloride solution, dried over anhydrous magnesium sulfate, and concentrated under reduced pressure. The residue was subjected to column chromatography (eluent: dichloromethane/methanol=95/5, v/v) to obtain 110 mg(0.21 mmol, Yield 75%) of the title compound.

$^1$H NMR(CDCl$_3$) δ 0.93–1.49(br, 5H), 2.50(s, 2H), 3.58 (d, 2H), 4.18(br, 2H), 5.05(s, 2H), 5.12(s, 2H), 6.63(s, 1H), 6.70(s, 1H), 7.09(s, 1H), 7.12 (s, 1H), 7.28–7.60(m, 10H), 7.89(d, 1H), 7.95(d, 1H), 8.10(d, 1H); FAB: 533 (M+H).

EXAMPLE 37

Synthesis of 1-[1-(1-Acetylpiperidin-4-yl)methyl-1H-imidazol-5-yl]methyl-3-(naphthalen-1-yl)carbonyl-1H-pyrrole(37)

110 mg(0.211 mmol) of the compound prepared in Example 36 was dissolved in 10ml of methanol, and 20 mg of Pd(OH)$_2$/C was added thereto. Then, the mixture was stirred for 3 hours under hydrogen atmosphere during which benzyloxycarbonyl group was removed. The reactants were filtered through a cellite to remove the catalyst and the solvent was removed under reduced pressure. The unpurified residue was dissolved in 5 ml of dimethylformamide, and 16.5 ml(0.232 mmol) of acetyl chloride was added thereto. The reaction solution was stirred for 30 minutes at room temperature and the solvent was removed under reduced pressure. To the residue was added 5 ml of saturated aqueous sodium bicarbonate solution, which was then extracted with 20 ml of ethyl acetate. The organic layer was washed with aqueous sodium chloride solution, dried over anhydrous magnesium sulfate and then concentrated under reduced pressure. The residue was subjected to column chromatography (eluent: dichloromethane/methanol=9/1, v/v) to obtain 20.3 mg(0.046 mmol, Yield 22%) of the title compound.

$^1$H NMR(CDCl$_3$) δ 1.11(m, 3H), 1.41(s, 3H), 2.06(s. 3H), 2.27(m, 1H), 2.78(m, 1H), 3.68(m, 2H), 4.58(d, 1H), 5.11(s, 2H), 6.69(s, 1H), 6.70(s, 1H), 7.11(s, 1H), 7.20(s, 1H), 7.50(m, 3H), 7.60(m, 1H), 7.90(m, 2H), 7.98(d, 1H), 8.12(d, 1H); FAB: 441 (M+1).

PREPARATION 6

Synthesis of 3-(4-Methylpiperazin-1-yl)carbonyl-4-(naphthalen-1-yl)-1H-pyrrole 234 mg(1 mmol) of the compound prepared in Preparation 2-3) was dissolved in 2 ml of dimethylformamide, 230 mg(1.2 mmol) of EDC and 162 mg(1.7 mmol) of HOBT were added thereto, and the resulting mixture was stirred for 5 minutes at 0° C. To this reaction solution was added 88 mg(1 mmol) of N-methylpiperazine, which was then stirred for 5 hours at room temperature. The solvent was removed under reduced pressure and 10 ml of saturated aqueous potassium carbonate solution was added to the residue. The resulting mixture was extracted with ethyl acetate, washed with aqueous sodium chloride solution and water and then concentrated. The concentrate was subjected to silica gel column chromatography(eluent: dichloromethane/methanol=85/15, v/v) to obtain 240 mg(0.75 mmol) of the title compound.

$^1$H NMR(CDCl$_3$) δ 1.13(br, 2H), 1.88(s, 3H), 1.75–2.08 (br, 2H), 2.98(br, 2H), 3.41(br, 2H), 6.85(s, 1H), 7.12(s, 1H), 7.35–7.58(m, 4H), 7.76(d, 1H), 7.82(d, 1H), 8.11(d, 1H), 10.20(br, 1H); FAB 320 (M+H).

PREPARATION 7

Synthesis of 3-{N-[2-(N,N-Dimethylamino)ethyl]-N-methyl}carbamoyl-4-(naphthalen-1-yl)-1H-pyrrole 234 mg(1 mmol) of the compound prepared in Preparation 2-3) was dissolved in 2 ml of dimethylformamide. 230 mg(1.2 mmol) of EDC, 101 mg(1 mmol) of triethylamine and 162 mg(1.7 mmol) of HOBT were added thereto and the resulting mixture was stirred for 5 minutes at 0° C. To the reaction solution was added 102 mg(1 mmol) of N,N,N'-trimethylethylenediamine, which was then stirred for 5 hours at room temperature. The solvent was removed under reduced pressure and 10 ml of saturated aqueous potassium carbonate solution was added to the residue. The resulting mixture was extracted with ethyl acetate, washed with aqueous sodium chloride solution and water, concentrated, and then subjected to silica gel column chromatography (eluent: dichloromethane/methanol=85/15, v/v) to obtain 257 mg(0.8 mmol) of the title compound.

$^1$H NMR(CDCl$_3$) δ 1.89(br, 3H), 2.15(br, 4H), 2.44(br, 2H), 2.75 (br, 1H), 3.0(br, 1H), 3.36(br, 2H), 6.84(s, 1H), 7.07(s, 1H), 7.38–7.43(m, 4H), 7.78(d, 1H), 7.83(d, 1H), 8.1(br, 1H), 10.05(br, 1H); FAB 322 (M+H).

EXAMPLE 38

Synthesis of 1-[1-(1-Benzyloxycarbonylpiperidin-4-yl)methyl-1H-imidazol-5-yl]methyl-3-(4-methylpiperazin-1-yl)carbonyl-4-(naphthalen-1-yl)-1H-pyrrole(38)

612 mg(2.0 mmol) of the compound prepared in Preparation 6 was dissolved in 10 ml of dimethylformamide, 264 mg(6.6 mmol) of sodium hydride(60%) was added thereto at 0° C., and then the resulting mixture was stirred for 5 minutes. 765 mg(2.2 mmol) of the compound prepared in Preparation 1-4) was added thereto and the mixture was stirred for 5 hours at room temperature. The solvent was removed by distillation under reduced pressure and 10 ml of water was added to the residue. The resulting solution was extracted twice with 20 ml of ethyl acetate, dried over magnesium sulfate, concentrated, and then subjected to silica gel column chromatography(eluent: dichloromethane/methanol=90/10, v/v) to obtain 930 mg(Yield 74%) of the title compound.

$^1$H NMR(CDCl$_3$) δ 0.86(m, 2H), 1.07(m, 2H), 1.24(m, 2H), 1.38(m, 1H), 1.52(m, 2H), 2.65(br, 2H), 3.00–3.50(br, 4H), 3.69(d, 2H), 4.16 (br, 2H), 5.09 (s, 2H), 5.11(s, 2H), 6.73 (d, 1H), 7.12 (s, 1H), 7.21 (s, 1H), 7.25–7.32 (m, 6H), 7.35–7.41 (m, 4H), 7.78(d, 1H), 7.83(d, 1H), 8.01(d, 1H); FAB (M+H) 631, $C_{38}H_{42}N_6O_3$.

EXAMPLE 39

Synthesis of 1-[1-(-Benzyloxycarbonylpiperidin-4-yl)methyl-1H-imidazol-5-yl]methyl-3-{N-[2-(N,N-dimethylamino)ethyl]-N-methyl}carbamoyl-4-(naphthalen-1-yl)-1H-pyrrole(39)

612 mg(2.0 mmol) of the compound prepared in Preparation 7 was dissolved in 10 ml of dimethylformamide, 264 mg(6.6 mmol) of sodium hydride(60%) was added thereto at 0° C., and then the resulting mixture was stirred for 5 minutes. 765 mg(2.2 mmol) of the compound prepared in Preparation 1-4) was added thereto and the mixture was stirred for 5 hours at room temperature. The solvent was removed by distillation under reduced pressure and 10 ml of water was added to the residue. This solution was extracted twice with 20 ml of ethyl acetate, dried over magnesium sulfate, concentrated and then subjected to silica gel column chromatography(eluent: dichloromethane/methanol=90/10, v/v) to obtain 870 mg(Yield 69%) of the title compound.

$^1$H NMR(CDCl$_3$+CD$_3$OD) δ 1.00(m, 2H), 1.31–1.40(m, 3H), 2.54–2.70(m, 9H), 3.50–3.80(m, 6H), 4.01(br, 2H), 4.50(s, 1H), 4.96(s, 2H), 5.07(s, 2H), 6.65(s, 1H), 7.01(s, 1H), 7.03(s, 1H), 7.13(s, 1H), 7.18–7.30(m, 7H), 7.45(s, 1H), 7.52(s, 1H), 7.64(d, 1H), 7.72(d, 1H), 7.80(d, 1H); FAB (M+H) 633: $C_{38}H_{44}N_6O_3$.

EXAMPLE 40

Synthesis of 1-[1-(1-Methoxycarbonylpiperidin-4-yl)methyl-1H-imidazol-5-yl]methyl-3-(4-methylpiperazin-1-yl)carbonyl-4-(naphthalen-1-yl)1H-pyrrole(40)

40-1) 3-(4-Methylpiperazin-1-yl)carbonyl-4-(naphthalen-1-yl)-1-[(piperidin-4-yl)methyl-1H-imidazol-5-yl]methyl-1H-pyrrole 227 mg(0.36 mmol) of the compound prepared in Example 38 was dissolved in 5 ml of methanol, 2 g of potassium hydroxide was added thereto, and the resulting mixture was reacted for 8 hours under reflux. The reaction solution was cooled down, extracted twice with 10 ml of ethyl acetate, dried over anhydrous sodium sulfate and then evaporated under reduced pressure to obtain the title compound in a yield of 80%.

$^1$H NMR(CDCl$_3$) δ 1.15(br, 2H), 1.48(d, 2H), 1.75–1.98 (m, 6H), 2.45(t, 2H), 2.91(br, 1H), 3.02(d, 2H), 3.31(br, 1H), 3.50–3.85(m, 7H), 5.10(s, 2H), 6.70(s, 1H), 7.09(m, 1H), 7.13(s, 1H), 7.30(t, 1H), 7.35–7.50(m, 4H), 7.74(d, 1H), 7.80(d, 1H), 8.01(d, 1H); FAB (M+H): 497, $C_{30}H_{36}N_6O$.

40-2) 1-[1-(1-Methoxycarbonylpiperidin-4-yl)methyl-1H-imidazol-5-yl]methyl-3-(4-methylpiperaziin-1-yl)carbonyl-4-(naphthalen-1-yl)-1H-pyrrole 30 mg(62 μmol) of the compound prepared in Example 40-1) was added to 2 ml of dichloromethane, and 5.4 mg(6.9 μmol) of methylchloroformate was added thereto using a syringe. This mixture was reacted for 2 hours, the solvent was removed under reduced pressure, and then the residue was subjected to silica gel column chromatography(eluent: dichloromethane/methanol=85/15, v/v) to obtain 27.8 mg(50 μmol, Yield 80%) of the title compound.

$^1$H NMR(CDCl$_3$) δ 1.06(m, 4H), 1.40(m, 1H), 1.51(d, 2H), 1.93(s, 3H), 2.02(br, 1H), 2.60(br, 3H), 2.98–3.60(br, 4H), 3.64(s, 3H), 3.69(d, 2H), 4.10(br, 2H), 5.14(s, 2H), 6.73(d, 1H), 7.12(s, 1H), 7.18(s, 1H), 7.30(t, 1H), 7.35–7.55 (m, 4H), 7.77(d, 1H), 7.82(d, 1H), 8.02(d, 1H); FAB (M+H): 555, $C_{32}H_{38}N_6O_3$.

EXAMPLE 41

Synthesis of 3-(4-Methylpiperazin-1-yl)carbonyl-1-[1-(1-methylsulfonylpiperidin-4-yl)methyl-1H-imidazol-5-yl]methyl-4-(naphthalen-1-yl)-1H-pyrrole(41)

30 mg(62 μmol) of the compound prepared in Example 40-1) was added to 2 ml of dichloromethane, and 7.8 mg(6.9 μmol) of methanesulfonyl chloride was added thereto using a syringe. This mixture was reacted for 2 hours, the solvent was removed under reduced pressure, and then the residue was subjected to silica gel column chromatography (eluent: dichloromethane/methanol=90/10, v/v) to obtain 25 mg(4.5 μmol, Yield 87%) of the title compound.

$^1$H NMR(CDCl$_3$) δ 1.03(m, 4H), 1.43(m, 1H), 1.52(d, 2H), 1.98(s, 3H), 2.03(br, 1H), 2.62(br, 3H), 2.04–3.65(br, 4H), 3.64(s, 3H), 3.69(d, 2H), 4.10(br, 2H), 5.13(s, 2H), 6.72(d, 1H), 7.11(s, 1H), 7.19(s, 1H), 7.31(t, 1H), 7.32–7.53 (m, 4H), 7.78(d, 1H), 7.83(d, 1H), 8.01(d, 1H); FAB (M+H): 575, $C_{32}H_{38}N_6O_3$.

EXAMPLE 42

Synthesis of 1-[1-(1-Acetylpiperidin-4-yl)methyl-1H-imidazol-5-yl]methyl-3-(4-methylpiperazin-1-yl)carbonyl-4-(naphthalen-1-yl)-1H-pyrrole(42)

30 mg(62 μmol) of the compound prepared in Example 40-1) was added to 2 ml of dichloromethane, and 5.4 mg(6.9 μmol) of acetyl chloride was added thereto using a syringe. This mixture was reacted for 2 hours, the solvent was removed under reduced pressure, and then the residue was subjected to silica gel column chromatography(eluent: dichloromethane/methanol=80/20, v/v) to obtain 26 mg(4.8 μmol, Yield 78%) of the title compound.

$^1$H NMR(CDCl$_3$) δ 1.00–1.12(m, 2H), 1.32–1.45(m, 2H), 1.52–1.58 (m, 2H), 1.90–2.10(m, 8H), 2.35(m, 1H), 2.93(t, 1H), 3.07(m, 1H), 3.10–3.70(br, 4H), 3.69(d, 1H), 7.75(d, 1H), 4.57(d, 1H), 5.12(s, 2H), 6.74(d, 1H), 7.12(d, 1H), 7.20(s, 1H), 7.34(d, 1H), 7.39–7.47(m, 4H), 7.78(d, 1H), 7.85(d, 1H), 8.01(d, 1H); FAB (M+H): 539, $C_{32}H_{38}N_6O_2$.

EXAMPLE 43

Synthesis of 3-(4-Methylpiperazin-1-yl)carbonyl-4-(naphthalen-1-yl)-1-{1-[1-(2-phenylethylcarbonyl)-piperidin-4-yl]methyl-1H-imidazol-5-yl}methyl-1H-pyrrole(43)

62 mg(125 μmol) of the compound prepared in Example 40-1) was dissolved in 2 ml of dichloromethane, and 22 mg(128 μmol) of 3-phenylpropionyl chloride was added thereto. This mixture was reacted for 3 hours, the solvent was removed, and then the residue was subjected to silica gel column chromatography(eluent: dichloromethane/methanol=95/5, v/v) to obtain 49 mg(Yield 62%) of the title compound.

$^1$H NMR(CDCl$_3$) δ 0.77(m, 1H), 0.90–1.20(m, 2H), 1.35 (m, 1H), 1.43(d, 1H), 1.51(d, 1H), 1.91(s, 3H), 1.80–2.00(br, 2H), 2.34(t, 1H), 2.55(m, 3H), 2.75(t, 1H), 2.85(br, 5H), 3.63(m, 3H), 3.72(d, 1H), 4.60(d, 1H), 5.11(s, 2H), 6.71(d, 1H), 7.09(d, 1H), 7.14–7.35(m, 7H), 7.38(m, 4H), 7.75(d, 1H), 7.81(d, 1H), 8.01(d, 1H); FAB (M+H): 629, $C_{39}H_{44}N_6O_2$.

EXAMPLE 44

Synthesis of 3-(4-Methylpiperazin-1-yl)carbonyl-4-(naphthalen-1-yl)-1-[1-(1-phenoxyacetylpiperidin-4-yl)methyl-1H-imidazol-5-yl]methyl-1H-pyrrole(44)

62 mg(125 μmol) of the compound prepared in Example 40-1) was dissolved in 2 ml of dichloromethane, and 23 mg(128 μmol) of phenoxyacetyl chloride was added thereto. This mixture was reacted for 3 hours, the solvent was removed, and then the residue was subjected to silica gel column chromatography(eluent: dichloromethane/methanol=95/5, v/v) to obtain 50 mg(Yield 63%) of the title compound.

$^1$H NMR(CDCl$_3$) δ 0.90–1.12(m, 4H), 1.28(m, 1H), 1.46 (d, 2H), 1.70–2.00(br, 1H), 1.84(s, 3H), 2.38(t, 1H), 2.86(t, 1H), 2.80–3.50(br, 5H), 3.59(m, 2H), 3.89(d, 1H), 4.48(d, 1H), 4.58(q, 2H), 5.05(s, 2H), 6.69(d, 1H), 6.86(d, 2H), 6.91(t, 1H), 7.04(d, 1H), 7.13(d, 1H), 7.20–7.30(m, 3H), 7.30–7.60(m, 4H), 7.71(d, 1H), 7.77(d, 1H), 7.98(d, 1H); FAB (M+H): 631, C$_{38}$H$_{42}$N$_6$O$_3$.

EXAMPLE 45

Synthesis of 3-(4-Methylpiperazin-1-yl)carbonyl-4-(naphthalen-1-yl)-1-{1-[1-(naphthalen-2-ylmethyloxy)carbonylpiperidin-4-yl]methyl-1H-imidazol-5-yl}methyl-1H-pyrrole(45)

1.19 g(7.52 mmol) of (naphthalen-2-yl)methanol was dissolved in 15 ml of toluene, and 1.04 g(7.53 mmol) of potassium dicarbonate was added thereto. To this solution was added 3.89 ml(1.93M in toluene) of phosgene solution at 0° C., and the whole solution was stirred for 2 hours at room temperature. The reactants were filtered to remove solid materials and then 0.108 g(0.222 mmol) of the compound prepared in Example 40-1) and 0.046 ml(0.33 mmol) of triethylamine were added thereto. The resulting mixture was stirred for 1 hour at room temperature, and distilled under reduced pressure to remove the solvent. 10 ml of saturated aqueous sodium bicarbonate solution was added to the residue, which was then extracted with ethyl acetate, dried over anhydrous magnesium sulfate and concentrated. The concentrate was subjected to silica gel column chromatography(eluent: dichloromethane/methanol=95/5, v/v) to obtain 65 mg(0.097 mmol, Yield 43%) of the title compound.

$^1$H NMR(CDCl$_3$) δ 0.94(m, 3H), 1.45(br, 3H), 2.61(m, 3H), 2.96 (s, 3H), 3.15(m, 2H), 3.75(m, 4H), 4.06(d, 2H), 4.71(br, 2H), 5.06(s, 2H), 5.18(s, 1H), 6.77(s, 1H), 7.15–8.00(m, 17H); FAB(M+H): 681, C$_{42}$H$_{44}$O$_3$N$_6$.

EXAMPLES 46 TO 48

The compounds represented in the following Table 5 were obtained according to the same procedure as Example 45.

TABLE 5-1

| COM. NO. | NMR(CDCl$_3$) | FAB (M + 1) |
|---|---|---|
| 46 | 0.89(d, 6H), 1.07(m, 2H), 1.37(m, 1H), 1.47–1.50(m, 5H), 1.65(m, 1H), 1.80–2.10(br, 4H), 2.59(br, 2H), 3.01–3.60(br, 5H), 3.90–4.20(m, 5H), 5.11(s, 2H), 6.73(d, 1H), 7.12(d, 1H), 7.18(s, 1H), 7.31(t, 1H), 7.31–7.54(m, 4H), 7.77 (d, 1H), 7.79(d, 1H), 8.01(d, 1H), C$_{36}$H$_{46}$N$_6$O$_3$ | 611 |
| 47 | 1.00–1.12(m, 3H), 1.38(m, 1H), 1.51(d, 3H), 1.95(s, 3H), 2.63(br, 3H), 3.00–3.60(br, 4H), 3.68(d, 2H), 4.12(r, 3H), 5.05(s, 2H), 5.11(s, 2H), 6.72(d, 1H), 7.00–7.07(m, 2H), 7.12(s, 1H), 7.20(s, 1H), 7.25–7.35(m, 3H), 7.36–7.52(m, 4H), 7.78(d, 1H), 7.83(d, 1H), 8.03(d, 1H), C$_{38}$H$_{41}$FN$_6$O$_3$ | 649 |

TABLE 5-2

| COM. NO. | NMR(CDCl$_3$) | FAB (M + 1) |
|---|---|---|
| 48 | 1.08(br, 2H), 1.20(d, 1H), 1.45–1.60(m, 4H), 3.25(br, 2H), 3.72(m, 2H), 4.01–4.21(br, 4H), 4.71(d, 1H), 5.15(s, 1H), 6.26–6.29(m, 1H), 6.60(d, 1H), 6.76(d, 1H), 7.14–7.45(m, 8H), 7.45–6.62(m, 3H), 7.63(s, 1H), 7.82(d, 1H), 7.83(d, 1H), 7.98(d, 1H), C$_{40}$H$_{44}$N$_6$O$_3$ | 657 |

EXAMPLE 49

Synthesis of 3-(4-Methylpiperazin-1-yl)carbonyl-4-(naphthalen-1-yl-1-{1-[1-(naphthalen-2-ylcarbonyl)piperidin-4-yl]methyl-1H-imidazol-5-yl}methyl-1H-pyrrole(49)

100 mg(0.206 mmol) of the compound prepared in Example 40-1) and 39 mg(0.22 mmol) of 2-naphthoic acid were dissolved in 1 ml of dimethylformamide. 59 mg(0.31 mmol) of EDC and 42 mg(0.31 mmol) of HOBT were added thereto, and the resulting mixture was stirred for 2 hours at room temperature. The solvent was removed by distillation under reduced pressure, then the residue was dissolved in ethyl acetate and washed with saturated aqueous sodium bicarbonate solution. The organic layer was dried over anhydrous magnesium sulfate, concentrated and subjected to silica gel column chromatography(eluent: dichloromethane/methanol=95/5, v/v) to obtain 88 mg(0.14 mmol, Yield 68%) of the title compound.

$^1$H NMR(CDCl$_3$) δ 1.05(br, 3H), 1.38(m, 1H), 1.56(d, 2H), 1.70–1.90(br, 6H), 2.36(br, 1H), 2.47(t, 1H), 2.82–3.07 (br, 3H), 3.32(br, 2H), 3.63(t, 2H), 4.07(br, 1H), 4.67(d, 1H), 5.09(s, 2H), 6.73(d, 1H), 6.84(d, 1H), 7.08(d, 1H), 7.31(d, 1H), 7.25–7.55(m, 10H), 7.58 (d, 1H), 7.73(d, 1H), 7.80(d, 1H), 8.02(d, 1H); FAB (M+1): 627, C$_{39}$H$_{42}$N$_6$O$_2$.

EXAMPLES 50 TO 51

The compounds represented in the following Table 6 were obtained according to the same procedure as Example 49 except that trans-cinnamic acid and 2-(2-propyl)thiazole-4-carboxylic acid, respectively, were used instead of 2-naphthoic acid.

TABLE 6

| COM. NO. | NMR(CDCl$_3$) | FAB (M + 1) |
|---|---|---|
| 50 | 1.08(br, 3H), 1.33–1.45(m, 1H), 1.58(d, 2H), 1.75–1.95(br, 2H), 1.83(s, 3H), 2.36(br, 1H), 2.47(br, 1H), 2.85–3.10(br, 3H), 3.15–3.50(br, 2H), 3.62–3.80(m, 2H), 4.02–4.15(br, H), 4.62–4.78(br, 1H), 5.10(s, 2H), 6.74(d, 1H), 6.82(d, 1H), 7.09(d, 1H), 7.18(s, 1H), 7.30–7.55(m, 10H), 7.60(d, 1H), 7.76(d, 1H), 7.80(d, 1H), 8.03(d, 1H), C$_{41}$H$_{42}$N$_6$O$_2$ | 627 |
| 51 | 1.01(br, H), 1.24(m, 2H), 1.37(d, 7H), 1.40–1.65(m, 3H), 1.70–2.02(m, 7H), 2.59(br, 1H), 2.92(br, 2H), 3.28(br, 2H), 3.71(d, 2H), 4.49(br, 1H), 4.65(br, H), 5.13(s, 2H), 6.73(d, 7.09(d, 1H), 7.18 (s, 1H), 7.32(d, 1H), 7.35–7.50(m, 4H), 7.68(s, 1H), 7.70(d, 1H), 7.84(d, 1H), 8.03(d, 1H), C$_{37}$H$_{43}$N$_7$O$_2$S | 650 |

EXAMPLE 52

Synthesis of 1-{1-[1-(N-Benzyl-N-methylcarbamoyl)piperidin-4-yl]methyl-1H-imidazol-5-yl}methyl-3-(4-methylpiperazin-1-yl)carbonyl-4-(naphthalen-1-yl-1H-pyrrole(52)

100 mg(0.206 mmol) of the compound prepared in Example 40-1) was dissolved in 1 ml of tetrahydrofuran and 27 mg(0.23 mmol) of N-benzyl-N-methylamine was added thereto at 0° C. 0.16 ml(1.93M in toluene) of phosgene solution was added dropwise thereto, and the resulting solution was stirred for 1 hour at room temperature. 1 ml of water was added to the solution, which was then extracted with ethyl acetate. The organic layer was dried over anhydrous magnesium sulfate, concentrated and subjected to silica gel column chromatography(eluent: dichloromethane/methanol=93/7, v/v) to obtain 86 mg(0.133 mmol, Yield 64%) of the title compound.

$^1$H NMR(CDCl$_3$+CF$_3$COOH) δ 1.24(m, 3H), 1.52(m, 4H), 2.44(s, 3H), 2.65–3.00(m, 8H), 3.04(s, 2H), 3.63(d, 2H), 4.00(br, 1H), 4.17(d, 2H), 4.32(s, 2H), 5.52(s, 2H), 7.21–7.63(m, 12H), 7.94(d, 1H), 7.96(d, 1H), 8.01(d, 1H), 9.06(s, 1H); FAB (M+1): 644, C$_{39}$H$_{45}$N$_7$O$_2$.

EXAMPLE 53

Synthesis of 1-{1-[1-(N,N-Dimethylcarbamoyl)piperidin-4-yl]methyl-1H-imidazol-5-yl}methyl-3-(4-methylpiperazin-1-yl)carbonyl-4-(naphthalen-1-yl)-1H-pyrrole(53)

The title compound represented in Table 7 was obtained according to the same procedure as Example 52 except that N,N-dimethylamine was used instead of N-benzyl-N-methylamine.

EXAMPLE 54

Synthesis of 3-(4-Methylpiperazin-1-yl)carbonyl-4-(naphthalen-1-yl)-1-{1-[1-(1,2,3,4-tetrahydroquinolin-1-ylcarbonyl)piperidin-4-yl]methyl-1H-imidazol-5-yl}methyl-1H-pyrrole(54)

The title compound represented in Table 7 was obtained according to the same procedure as Example 52 except that 1,2,3,4-tetrahydroquinoline was used instead of N-benzyl-N-methylamine.

EXAMPLE 55

Synthesis of 3-(4-Methylpiperazin-1-yl)carbonyl-4-(naphthalen-1-yl)-1-{1-[1-(1,2,3,4-tetrahydroisoquinolin-2-ylcarbonyl)piperidin-4-yl]methyl-1H-imidazol-5-yl}methyl-1H-pyrrole(55)

The title compound represented in Table 7 was obtained according to the same procedure as Example 52 except that 1,2,3,4-tetrahydroisoquinoline was used instead of N-benzyl-N-methylamine.

TABLE 7

| COM. NO. | NMR(CDCl$_3$) | FAB MS (M + 1) |
|---|---|---|
| 53 | 1.00–1.30(m, 3H), 1.31–1.67(m, 3H), 1.70–2.05(m, 6H),2.59(m, 2H), 2.74(s, 6H), 2.89(m, 2H), 3.20–3.50(m, 2H), 3.68(m, 4H), 5.10(s, 2H), 6.74(d, 1H), 7.12(d, 1H), 7.20(s, 1H), 7.34(d, 1H), 7.39–7.47(m, 4H), 7.78(d, 1H), 7.85(d, 1H), 8.01(d, 1H), C$_{33}$H$_{41}$N$_7$O$_2$ | 568 |
| 54 | 1.03–1.30(m, 4H), 2.31–2.51(m, 3H), 1.70–2.20(m, 10H), 2.57(t, 2H), 2.72(t, 1H), 2.90(br, 2H), 3.31(br, 2H), 3.54(t, 1H), 3.66(m, 2H), 3.81(d, 1H), 5.11(s, 2H), 6.68(d, 1H), 6.83(t, 1H), 6.92(d, 1H), 7.1(m, 2H), 7.12(d, 1H), 7.18(s, 7.31(d, 1H), 7.44(m, 4H), 7.76(d, 1H), 7.82(d, 1H), 8.02(d, 1H); C$_{40}$H$_{45}$N$_7$O$_2$ | 656 |

TABLE 7-continued

| COM. NO. | NMR(CDCl$_3$) | FAB MS (M + 1) |
|---|---|---|
| 55 | 0.9–2.1(m, 12H), 2.72(t, 2H), 2.80–3.95(m, 12H), 4.37(s, 2H) 5.12(s, 2H), 6.72(s, 1H), 7.00–7.70(m, 1H), 7.78(d, 1H), 7.82(d, 1H), 8.05(d, 1H); C$_{40}$H$_{45}$N$_7$O$_2$ | 656 |

EXAMPLE 56

Synthesis of 1-{1-[1-(4-Biphenylmethyl)piperidin-4-yl]methyl-1H-imidazol-5-yl}methyl-3-(4-methylpiperazin-1-yl)carbonyl-4-(naphthalen-1-yl)-1H-pyrrole(56)

100 mg(0.206 mmol) of the compound prepared in Example 40-1) was dissolved in 3 ml of tetrahydrofuran, 45 mg(0.24 mmol) of 4-phenylbenzaldehyde and 52 mg(0.24 mmol) of sodium triacetoxyborohydride were added thereto, and the resulting solution was stirred for 10 hour at room temperature. 1 ml of 1N HCl-methanol solution was added to the reaction solution, which was then stirred for 30 minutes, basified and extracted with ethyl acetate. The organic layer was dried over anhydrous magnesium sulfate, concentrated and subjected to silica gel column chromatography(eluent: dichloromethane/methanol=93/7, v/v) to obtain 100 mg(0.151 mmol, Yield 75%) of the title compound.

FAB MS(M+1): 663.

EXAMPLE 57

Synthesis of 3-(4-Methylpiperazin-1-yl)carbonyl-4-(naphthalen-1-yl)-1-{1-[1-(4-phenoxybenzyl)piperidin-4-yl]methyl-1H-imidazol-5-yl}methyl-1H-pyrrole(57)

The title compound was obtained according to the same procedure as Example 56 except that 4-phenoxybenzaldehyde was used instead of 4-phenylbenzaldehyde.

FAB MS(M+1): 679.

EXPERIMENTAL EXAMPLE 1

Analysis of in vitro Inhibitory Activity for Ras Farnesyl Transferase

In the present experiment, Ras farnesyl transferase produced by genetic recombination techniques according to the improved Pompliano's method (Pompliano et al., Biochemistry, 1992, 31, 3800) was used, and Ras substrate (Ras-CVLS) protein described in Korean Patent Appln. No. 97-14409 was used after it has been purified according to the known method(see, Chung et al., Biochimica et Biophysica Acta, 1992, 278, 1129).

The enzyme reaction was performed in 50 μl of 50 mM Soduam HEPES buffer solution containing 25 mM of potassium chloride, 25 mM of magnesium chloride, 10 mM of DTT and 50 μM of zinc chloride. 1.5 μM of Ras substrate protein, 0.15 μM of tritium-farnesylpyrophosphate and 4.5 nM of farnesyl transferase were used.

More specifically, in the initial step, farnesyl transferase was added to the above buffer solution, reaction was maintained for 30 minutes at 37° C. and then the reaction was stopped by adding 1 ml of ethanol solution containing 1M HCl. The formed precipitates were adsorbed to GF/B filter using Hopper harvestor(Hopper #FH 225V) for filter-binding, washed with ethanol, and then radioactivity of the dried filter was measured using LKB β counter. Enzyme titer was measured in the unsaturated state of substrate where the concentrations of Ras substrate protein and farnesyl transferase have quantitative relationship. The compound according to the present invention dissolved in dimethyl sulfoxide (DMSO) was added to the reaction solution in an amount of less than 5% of the total reaction solution, and then the enzyme inhibitory activity thereof was measured. The enzyme inhibitory activity was represented by percentage of the amount of farnesyl incorporated into the Ras substrate protein in the presence of the test compound to that in the absence of the test compound. $IC_{50}$ of the test compound was defined as the concentration at which 50% of the enzyme activity was inhibited.

To evaluate the selective enzyme inhibitory activity of the compound according to the present invention, inhibitory activity on geranylgeranyl transferase was measured. Geranylgeranyl transferase was purified from bovine brain according to the method modified from Schaber's method (Schaber et al., J. Biol. Chem. 1990, 265, 14701), and substantially the same experimental procedure as that for farnesyl transferase was performed on geranylgeranyl pyrophosphate and Ras-CVIL substrate protein.

The test results are represented in the following Table 8.

EXPERIMENTAL EXAMPLE 2

Analysis of in vivo Inhibitory Activity for Ras Farnesyl Transferase

In the present experiment, Rat2 cell line which expresses C-Harvey-Ras protein having transforming activity and Rat2 cell line(Korean patent application No. 97-14409) which is transformed with fused protein of H-Ras substituted with polybasic lysine domain at C-terminus of K-Ras were used. The experiment was performed by the modified Declue's method(Declue. J. E. et al., Cancer Research, 1991, 51, 712). Hereinafter, the experimental method will be described in more detail.

$3 \times 10^5$ cells of transformed Rat2 fibroblast cell line were sprayed on 60 mm cell cultivation dish and cultivated for 48 hours in a cell incubator at 37° C. and after 50% or more of density was reached, it was treated with the test compounds. The compound according to the present invention dissolved in dimethylsulfoxide(DMSO) was used. 1% concentration of dimethylsulfoxide was used in both control and test groups. After 4 hours from the treatment with the compound, methionine labeled with 150 $\mu$Ci of radioactive isotope [$^{35}$S] per 1 ml of medium was added and after cultivating for 20 hours, the cells were washed with physiological saline water. The cells were lysed using 1 ml of cold cell lysis buffer solution(50 mM of Sodium HEPES buffer solution containing 5 mM of magnesium chloride, 1 mM of DTT, 1% NP 40, 1 mM of EDTA, 1 mM of PMSF, 2 $\mu$M of leupeptin, 2 $\mu$M of pepstatin A and 2 $\mu$M of antipain) and the supernatant wherein the cells were lysed was obtained by high-velocity centrifugation of 12,000 g×5 minutes. The amount of radioisotope in the supernatant was measured and standardized to obtain a quantitative result in immunoprecipitation reaction and then, Y13-259, a monoclonal antiboby specifically binding to Ras protein(Furth, M. E. et al., J. Virol, 1982, 43, 294) was added and reacted for 15 hours at 4° C. Protein A(combined with goat anti-murine imunoglobulin antibody)-agarose suspension was added to the solution and reacted for 1 hour at 4° C. and then, to remove the unspecific binding product, immunoprecipitates were washed with a buffer solution (50 mM Tris chloride buffer solution containing 50 mM of sodium chloride, 0.5% of sodium dioxycholate, 0.5% of NP 40 and 0.1% of SDS). The precipitates were added to a buffer solution for electrophoresis and boiled and then, electrophoresis was performed using 13.5% of SDS polyacrylamide gel. After electrophoresis, the gel was fixed and dried. Then, the gel was exposed to X-ray film, developed and printed. From the result of the experiment, intensities of band of protein combined with or without farnesyl of Ras protein were measured, and the concentration of the test compound inhibiting 50% of farnesyl binding was defined as $CIC_{50}$, an in vivo Ras farnesyl transferase inhibitory activity. The test results are shown in the following Table 8.

TABLE 8-1

| COM. NO. | H-Ras $IC_{50}(\mu M)$ | H-Ras $CIC_{50}(\mu M)$ | K-Ras $IC_{50}(\mu M)$ | K-Ras $CIC_{50}(\mu M)$ |
|---|---|---|---|---|
| 1 | 0.0085 | 0.1 | 2.4 | 1–10 |
| 2 | 0.009 | 0.1 | 6 | 10–100 |
| 3 | 0.001 | 0.01–0.1 | 0.016 | 10–50 |
| 4 | 0.0036 | 0.01–0.1 | 0.026 | 10–50 |
| 5 | 0.0025 | 0.01–0.1 | 0.01–0.1 | 1–10 |
| 6 | 0.008 | 0.01–0.1 | 0.01–1 | 1–10 |
| 7 | 0.0018 | 0.01–0.1 | 0.01–0.1 | 10–100 |
| 8 | 0.0012 | 0.01–0.1 | 0.01–0.1 | 10–50 |
| 9 | 0.001–0.01 | 0.01–0.1 | 0.01–1 | 1–50 |
| 10 | 0.001–0.01 | 0.01–0.1 | 0.01–1 | 1–50 |
| 11 | 0.001–0.01 | 0.01–0.1 | 0.01–1 | 1–50 |
| 12 | 0.001–0.01 | 0.01–0.01 | 0.01–1 | 1–50 |
| 13 | 0.001–0.01 | 0.01–0.1 | 0.01–1 | 1–50 |
| 14 | 0.0021 | 0.01–0.1 | 0.01–1 | 1–50 |
| 15 | 0.001 | 0.01–0.1 | 0.01–1 | 1–50 |
| 16 | 0.001–0.01 | 0.01–0.1 | 0.01–1 | 1–50 |
| 17 | 0.001–0.01 | 0.01–0.1 | 0.01–1 | 10–100 |
| 18 | 0.001 | 0.01–0.1 | 0.01–1 | 1–50 |
| 19 | 0.007 | 0.01 | 0.02 | 1–10 |
| 20 | 0.006 | 0.01 | 0.01 | 1–10 |
| 21 | 0.01–0.1 | 0.01–0.1 | 0.05 | 1–10 |
| 22 | 0.009 | 0.01–0.1 | 0.02 | 1–10 |
| 23 | 0.008 | 0.01–0.1 | 0.02 | 1–10 |
| 24 | 0.006 | 0.01–0.1 | 0.015 | 1–10 |

TABLE 8-2

| COM. NO. | H-Ras $IC_{50}(\mu M)$ | H-Ras $CIC_{50}(\mu M)$ | K-Ras $IC_{50}(\mu M)$ | K-Ras $CIC_{50}(\mu M)$ |
|---|---|---|---|---|
| 25 | 0.006 | 0.0–0.1 | 0.027 | 1–10 |
| 26 | 0.004 | 0.01–0.1 | 0.01–0.1 | 10–50 |
| 27 | 0.009 | 0.01–0.1 | 0.015 | 1–10 |
| 28 | 0.012 | 0.01–0.1 | 0.008 | 1–10 |
| 29 | 0.0025 | 0.01–0.1 | 0.01–0.1 | 10–50 |
| 30 | 0.0025 | 0.01–0.1 | 0.006 | 1–10 |
| 31 | 0.004 | 0.01–0.1 | 0.02 | 10–50 |
| 32 | 0.002 | 0.01–0.1 | 0.012 | 1–10 |
| 33 | 0.005 | 0.01–0.1 | 0.01–0.1 | 1–10 |
| 34 | 0.011 | 0.01–0.1 | 0.01–0.1 | 1–10 |
| 35 | 0.006 | 0.01–0.1 | 0.01–0.1 | 1–10 |
| 36 | 0.2 | 10 | >100 | 50 |
| 37 | 0.35 | 1–10 | 10–100 | 10–50 |
| 38 | 0.0038 | 0.0125 | 0.015 | 2.5 |
| 39 | 0.3 | 1 | 1.5 | 30–100 |
| 40 | 0.0016 | 0.03 | 0.0042 | 10–50 |
| 41 | 0.003 | 0.05 | 0.01 | 10–50 |
| 42 | 0.0012 | 0.025 | 0.006 | 10–50 |
| 43 | 0.002 | 0.05 | 0.01 | 10–50 |
| 44 | 0.002 | 0.05 | 0.011 | 10–50 |
| 45 | 0.0018 | 0.035 | 0.012 | 10 |
| 46 | 0.0022 | 0.025 | 0.016 | 10–50 |

TABLE 8-2-continued

| COM. NO. | H-Ras IC$_{50}$($\mu$M) | H-Ras CIC$_{50}$($\mu$M) | K-Ras IC$_{50}$($\mu$M) | K-Ras CIC$_{50}$($\mu$M) |
|---|---|---|---|---|
| 47 | 0.0033 | 0.0125 | 0.006 | 4 |
| 48 | 0.0033 | 0.0125 | 0.007 | 1 |

TABLE 8-3

| COM. NO. | H-Ras IC$_{50}$($\mu$M) | H-Ras CIC$_{50}$($\mu$M) | K-Ras IC$_{50}$($\mu$M) | K-Ras CIC$_{50}$($\mu$M) |
|---|---|---|---|---|
| 49 | 0.0018 | 0.35 | 0.012 | 10 |
| 50 | 0.0017 | 0.03 | 0.008 | 10–50 |
| 51 | 0.003 | 0.005 | 0.01 | 10–50 |
| 52 | 0.0023 | 0.05 | 0.01 | 10–50 |
| 53 | 0.003 | 0.05 | 0.0085 | 10–50 |
| 54 | 0.011 | 0.025 | 0.04 | 10–50 |
| 55 | 0.002 | 0.025 | 0.04 | 10–50 |
| 56 | 0.005 | 0.05 | 0.02 | 5 |
| 57 | 0.011 | 0.025 | 0.01 | 10 |

What is claimed is:

1. A piperidine derivative represented by the following formula (1):

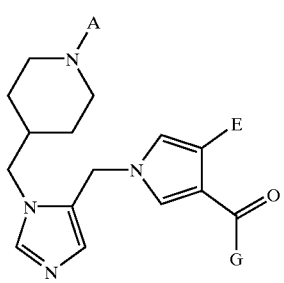

in which

A represents hydrogen, lower alkyl, or

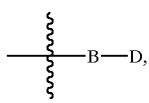

wherein

B represents CH$_2$, C=O or SO$_2$, and

D represents a radical selected from the following group:

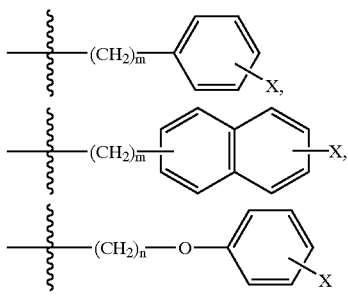

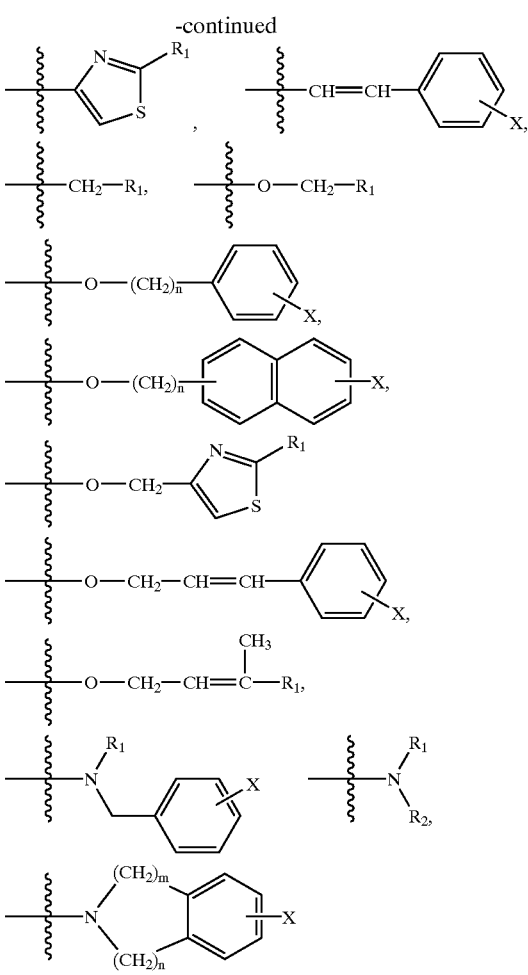

In the definition for the substituent D, m denotes an integer of 0 to 3, n denotes an integer of 1 to 3, X represents hydrogen, phenyl, phenoxy, lower alkyl, lower alkoxy, halogen, nitro, or amino which is optionally substituted by benzyl or lower alkyl, R$_1$ and R$_2$ independently of one another represent hydrogen, lower alkyl, C$_3$–C$_6$-cycloalkyl, lower alkyl substituted by C$_3$–C$_6$-cycloalkyl, aryl or heteroaryl, E represents hydrogen, phenyl, naphthyl or

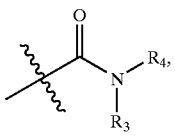

wherein

R$_3$ and R$_4$ independently of one another represent hydrogen, lower alkyl, aril or,

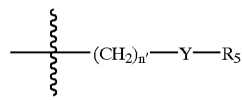

(wherein Y represents O or S, n' denotes an integer of 2 to 4, and R$_5$ represents lower alkyl), G represents a radical selected from the following group:

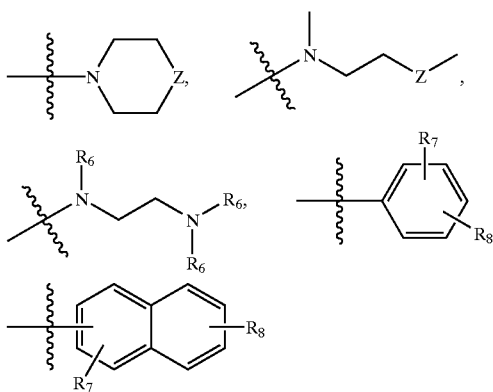

wherein

Z represents O, S, SO$_2$ or N—R$_6$ (wherein R$_6$ represents hydrogen or lower alkyl), R$_7$ and R$_8$ independently of one another represent hydrogen, lower alkyl, lower alkoxy, halogen, cyano, hydroxycarbonyl, aminocarbonyl, aminothiocarbonyl, hydroxy, phenyl or phenoxy, or a pharmaceutically acceptable salt thereof.

2. The compound of claim 1 wherein

A represents hydrogen, lower alkyl, or

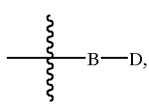

wherein

B represents CH$_2$, C═O or SO$_2$,

D represents a radical selected from the following group:

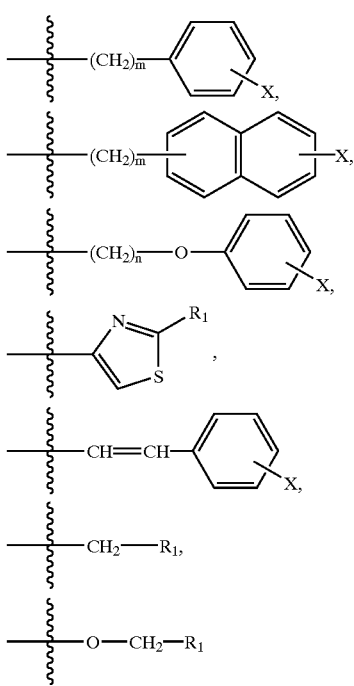

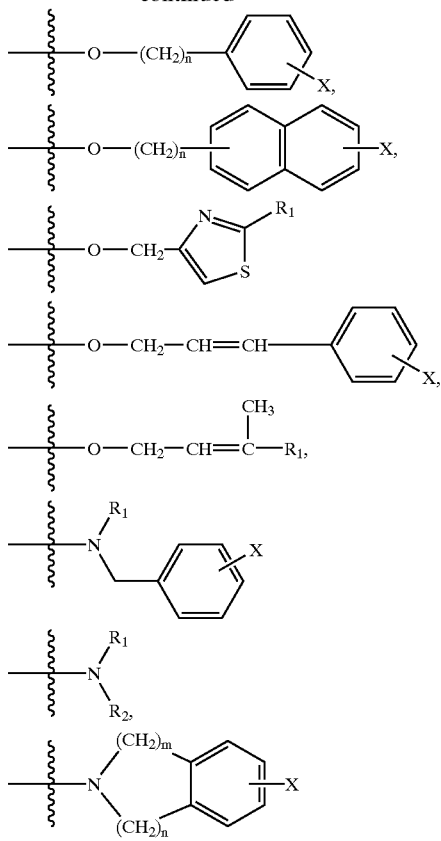

In the definition for the substituent D, m denotes an integer of 0 to 1, n denotes an integer of 1 to 2, X represents hydrogen, R$_1$ and R$_2$ independently of one another represent hydrogen or lower alkyl, E represents hydrogen, phenyl, naphthyl, or

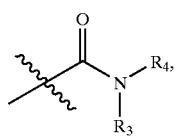

wherein

R$_3$ and R$_4$ independently of one another represent hydrogen, lower alkyl, or 2-methoxyethyl, G represents a radical selected from the following group:

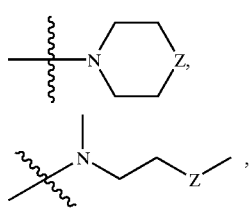

-continued

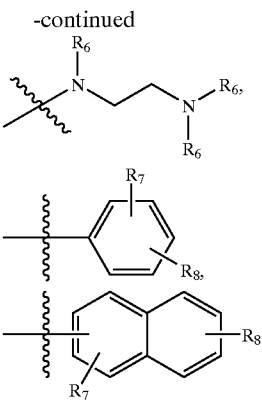

wherein
Z represents O or N—$R_6$ (wherein $R_6$ represents methyl),
$R_7$ and $R_8$ independently of one another represent hydrogen.

3. The compound of claim 1 which is selected from a group consisting of:

1-[1-(1-benzyloxycarbonyl-piperidin-4-ylmethyl)-1H-imidazol-5-ylmethyl]-3-(morpholin-4-yl)carbonyl-4-(naphthalen-1-yl)-1H-pyrrole(1);

3-(morpholin-4-yl)carbonyl-4-(naphthalen-1-yl)-1-[1-(piperidin-4-ylmethyl)-1H-imidazol-5-ylmethyl]-1H-pyrrole(2);

1-[1-(1-acetylpiperidin-4-ylmethyl)-1H-imidazol-5-ylmethyl]-3-(morpholin-4-yl)carbonyl-4-(naphthalen-1-yl)-1H-pyrrole(3);

1-[1-(1-methylsulfonyl-piperidin-4-ylmethyl)-1H-imidazol-5-ylmethyl]-3-(morpholin-4-yl)carbonyl-4-(naphthalen-1-yl)-1H-pyrrole(4);

1-[1-(1-benzyloxycarbonyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(5);

3-[N-(2-methoxyethyl)-N-methyl]carbamoyl-4-(naphthalen-1-yl)-1-[1-(piperidin-4-ylmethyl)-1H-imidazol-5-ylmethyl]-1H-pyrrole(6);

1-[1-(1-acetyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(7);

3-[N-(2-methoxyethyl)-N-methyl]carbamoyl-1-[1-(1-methylsulfonyl-piperidin-4-ylmethyl)-1H-imidazol-5-ylmethyl]-4-(naphthalen-1-yl)-1H-pyrrole(8);

1-{1-[1-(N-benzylcarbamoyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(9);

1-{1-[1-(N-butylcarbamoyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(10);

1-{1-[1-(N-cyclohexylcarbamoyl)-piperidin-4-ylmethyl]-1H-imidazol-5-ylmethyl}-3-[N-(2-methoxyethyl)-N-methyl]carbamoyl-4-naphthalen-1-yl)-1H-pyrrole(11);

1-[1-(1-heptanoyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(12);

1-{1-[1-(4-methoxybenzylcarbonyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(13);

3-[N-(2-methoxyethyl)-N-methyl]carbamoyl-4-(naphthalen-1-yl)-1-[1-(1-phenoxyacetyl-piperidin-4-ylmethyl)-1H-imidazol-5-ylmethyl]-1H-pyrrole(14);

3-[N-(2-methoxyethyl)-N-methyl]carbamoyl-4-(naphthalen-1-yl)-1-{1-[1-(2-phenylethylcarbonyl)-piperidin-4-ylmethyl]-1H-imidazol-5-ylmethyl}-1H-pyrrole(15);

1-{1-[1-(4-biphenylacetyl)-piperidin-4-ylmethyl]-1H-imidazol-5-ylmethyl}-3-[N-(2-methoxyethyl)-N-methyl]carbamoyl-4-(naphthalen-1-yl)-1H-pyrrole(16);

1-[1-(1-methoxycarbonyl-piperidin-4-ylmethyl)-1H-imidazol-5-ylmethyl]-3-[N-(2-methoxyethyl)-N-methyl]carbamoyl-4-(naphthalen-1-yl)-1H-pyrrole(17);

3-[N-(2-methoxyethyl)-N-methyl]carbamoyl-4-(naphthalen-1-yl)-1-[1-(1-propionyl-piperidin-4-ylmethyl)-1H-imidazol-5-ylmethyl]-1H-pyrrole(18);

3-[N-(2-methoxyethyl)-N-methyl]carbamoyl-4-(naphthalen-1-yl)-1-{1-[1-(naphthalen-1-ylmethyloxycarbonyl)piperidin-4-ylmethyl]-1H-imidazol-5-ylmethyl}-1H-pyrrole(19);

3-[N-(2-methoxyethyl)-N-methyl]carbamoyl-4-(naphthalen-1-yl)-1-{1-[1-(naphthalen-2-ylmethyloxycarbonyl)piperidin-4-ylmethyl]-1H-imidazol-5-ylmethyl}-1H-pyrrole(20), 1-{1-[1-(3,7-dimethylocta-2,6-dien-1-yloxycarbonyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(21), 3-[N-(2-methoxyethyl)-N-methyl]carbamoyl-1-{1-[1-(3-methyl-2-buten-1-yloxycarbonyl)piperidin-4-ylmethyl]-1H-imidazol-5-ylmethyl}-4-(naphthalen-1-yl)-1H-pyrrole(22), 3-[N-(2-methoxyethyl)-N-methyl]carbamoyl-1-{1-[1-(3-methylbutan-1-yloxycarbonyl)piperidin-4-ylmethyl]-1H-imidazol-5-ylmethyl}-4-(naphthalen-1-yl)-H-pyrrole(23), 1-{1-[1-(4-fluorobenzyloxycarbonyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(24), 1-{1-[1-(cinnamyloxycarbonyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(25), 1-{1-[1-(2-isopropylthiazol-4-ylmethyloxycarbonyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(26), 3-[N-(2-methoxyethyl)-N-methyl]carbamoyl-4-(naphthalen-1-yl)-1-{1-[1-(naphthalen-2-ylcarbonyl)piperidin-4-ylmethyl]-1H-imidazol-5-ylmethyl}-1H-pyrrole(27);

1-[1-(1-cinnamoylpiperidin-4-ylmethyl)-1H-imidazol-5-ylmethyl]-3-[N-(2-methoxyethyl)-N-methyl]carbamoyl-4-(naphthalen-1-yl)-1H-pyrrole(28), 1-{1-[1-(2-isopropylthiazol-4-ylcarbonyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(29), 1-{1-[1-(N-benzyl-N-methylcarbamoyl)piperidin-4-ylmethyl]-1H-imidazol-5-ylmethyl}-3-[N-(2-methoxyethyl)-N-methyl]carbamoyl-4-(naphthalen-1-yl)-1H-pyrrole(30);

3-[N-(2-methoxyethyl)-N-methyl]carbamoyl-4-(naphthalen-1-yl)-1-{1-[1-(1,2,3,4-tetrahydroquinolin-1-ylcarbonyl)piperidin-4-ylmethyl]-1H-imidazol-5-ylmethyl}-1H-pyrrole(31);

3-[N-(2-methoxyethyl)-N-methyl]carbamoyl-4-(naphthalen-1-yl)-1-{1-[1-(1,2,3,4-tetrahydroisoquinolin-2-ylcarbonyl)piperidin-4-ylmethyl]-1H-imidazol-5-ylmethyl}-1H-pyrrole(32);

1-{1-[1-(4-biphenylmethyl)piperidin-4-ylmethyl]-1H-imidazol-5-ylmethyl}-3-[N-(2-methoxyethyl)-N-methyl]carbamoyl-4-(naphthalen-1-yl)-1H-pyrrole (33);

3-[N-(2-methoxyethyl)-N-methyl]carbamoyl-4-naphthalen-1-yl)-1-{1-[1-(4-phenoxybenzyl)piperidin-4-ylmethyl]-1H-imidazol-5-ylmethyl}-1H-pyrrole (34);

1-[-(1-isobutoxycarbonyl-piperidin-4-ylmethyl)-1H-imidazol-5-ylmethyl]-3-[N-(2-methoxyethyl)-N-methyl]carbamoyl-4-(naphthalen-1-yl)-1H-pyrrole (35);

1-{1-[1-(benzyloxycarbonyl)piperidin-4-yl]methyl-1H-imidazol-5-yl}methyl-3-(naphthalen-1-yl)carbonyl-1H-pyrrole(36);

1-[1-(1-acetylpiperidin-4-yl)methyl-1H-imidazol-5-yl]methyl-3-(naphthalen-1-yl)carbonyl-1H-pyrrole(37);

1-[1-(1-benzyloxycarbonylpiperidin-4-yl)methyl-1H-imidazol-5-yl]methyl-3-(4-methylpiperazin-1-yl)carbonyl-4-(naphthalen-1-yl)-1H-pyrrole(38);

1-[1-(1-benzyloxycarbonylpiperidin-4-yl)methyl-1H-imidazol-5-yl]methyl-3-{N-[2-(N,N-dimethylamino)ethyl]-N-methyl}carbamoyl-4-(naphthalen-1-yl)-1H-pyrrole(39);

1-[1-(1-methoxycarbonylpiperidin-4-yl)methyl-1H-imidazol-5-yl]methyl-3-(4-methylpiperazin-1-yl)carbonyl-4-(naphthalen-1-yl)-1H-pyrrole(40);

3-(4-methylpiperazin-1-yl)carbonyl-1-[1-(1-methylsulfonylpiperidin-4-yl)methyl-1H-imidazol-5-yl]methyl-4-(naphthalen-1-yl)-1H-pyrrole(41);

1-[1-(1-acetylpiperidin-4-yl)methyl-1H-imidazol-5-yl]methyl-3-(4-methylpiperazin-1-yl)carbonyl-4-(naphthalen-1-yl)-1H-pyrrole(42);

3-(4-methylpiperazin-1-yl)carbonyl-4-(naphthalen-1-yl)-1-{1-[1-(2-phenylethylcarbonyl)-piperidin-4-yl]methyl-1H-imidazol-5-yl}methyl-1H-pyrrole(43);

3-(4-methylpiperazin-1-yl)carbonyl-4-(naphthalen-1-yl)-1-[1-(1-phenoxyacetyl piperidin-4-yl)methyl-1H-imidazol-5-yl]methyl-1H-pyrrole(44);

3-(4-methylpiperazin-1-yl)carbonyl-4-(naphthalen-1-yl)-1-{1-[1-(naphthalen-2-ylmethyloxy)carbonylpiperidin-4-yl]methyl-1H-imidazol-5-yl}methyl-1H-pyrrole(45);

1-{1-[1-(3-methylbutyloxy)carbonylpiperidin-4-yl]methyl-1H-imidazol-5-yl}methyl-3-(4-methylpiperazin-1-yl)carbonyl-4-(naphthalen-1-yl)-1H-pyrrole(46);

1-{1-[1-(4-fluorobenzyloxy)carbonylpiperidin-4-yl]methyl-1H-imidazol-5-yl}methyl-3-(4-methylpiperazin-1-yl)carbonyl-4-(naphthalen-1-yl)-1H-pyrrole(47), 1-{1-[1-(cinnamyloxycarbonyl)piperidin-4-yl]methyl-1H-imidazol-5-yl}methyl-3-(4-methylpiperazin-1-yl)carbonyl-4-(naphthalen-1-yl)-1H-pyrrole(48), 3-(4-methylpiperazin-1-yl)carbonyl-4-(naphthalen-1-yl)-1-{1-[1-(naphthalen-2-ylcarbonyl)piperidin-4-yl]methyl-1H-imidazol-5-yl}methyl-1H-pyrrole(49);

1-{1-[1-(cinnamoyl)piperidin-4-yl]methyl-1H-imidazol-5-yl}methyl-3-(4-methylpiperazin-1-yl)carbonyl-4-(naphthalen-1-yl)-1H-pyrrole(50);

1-{1-[1-(2-isopropylthiazol-4-ylcarbonyl)piperidin-4-yl]methyl-1H-imidazol-5-yl}methyl-3-(4-methylpiperazin-1-yl)carbonyl-4-(naphthalen-1-yl)-1H-pyrrole(51);

1-{1-[1-(N-benzyl-N-methylcarbamoyl)piperidin-4-yl]methyl-1H-imidazol-5-yl}methyl-3-(4-methylpiperazin-1-yl)carbonyl-4-(naphthalen-1-yl)-1H-pyrrole(52);

1-{-[1-(N,N-dimethylcarbamoyl)piperidin-4-yl]methyl-1H-imidazol-5-yl}methyl-3-(4-methylpiperazin-1-yl)carbonyl-4-(naphthalen-1-yl)-1H-pyrrole(53);

3-(4-methylpiperazin-1-yl)carbonyl-4-(naphthalen-1-yl)-1-{1-[1-(1,2,3,4-hydroquinolin-1-ylcarbonyl)piperidin-4-yl]methyl-1H-imidazol-5-yl}methyl-1H-pyrrole(54);

3-(4-methylpiperazin-1-yl)carbonyl-4-(naphthalen-1-yl)-1-{1-[1-( 1,2,3,4-tetrahydroisoquinolin-2-ylcarbonyl)piperidin-4-yl]methyl-1H-imidazol-5-yl}methyl-1H-pyrrole(55);

1-{1-[1-(4-biphenylmethyl)piperidin-4-yl]methyl-1H-imidazol-5-yl}methyl-3-(4-methylpiperazin-1-yl)carbonyl-4-(naphthalen-1-yl)-1H-pyrrole(56); and 3-(4-methylpiperazin-1-yl)carbonyl-4-(naphthalen-1-yl)-1-{1-[1-(4-phenoxybenzyl)piperidin-4-yl]methyl-1H-imidazol-5-yl}methyl-1H-pyrrole(57).

4. A process for preparing a piperidine derivative of formula (1) as defined in claim 1 wherein (a) a compound represented by the following formula (2a)

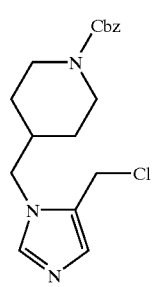

(2a)

wherein Cbz represents benzyloxycarbonyl, is reacted in a solvent in the presence of a base with a compound represented by the following formula (3):

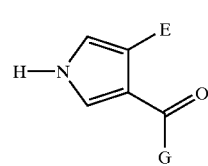

(3)

wherein E and G are defined as in claim 1, then the protecting group Cbz is eliminated to produce a compound represented by the following formula (1a):

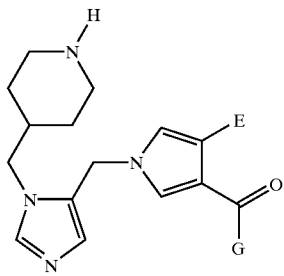

wherein E and G are defined as in claim 1;

(b) the compound of formula (1a) is reacted in a solvent with a compound represented by the following formula (4):

A'—W (4)

wherein A' is the same as A defined in claim 1 except that A' is not hydrogen, and W represents hydrogen, hydroxy, or reactive leaving group, to produce a compound represented by the following formula (1b):

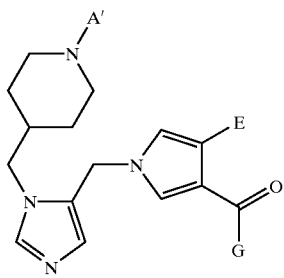

wherein A' is defined as previously described and E and G are defined as in claim 1; or (c) the compound of formula (1a) is reacted in a solvent with a compound represented by the following formula (5):

A"—N=C=O (5)

wherein A" represents lower alkyl, benzyl or $C_3$–$C_6$-cycloalkyl, to produce a compound represented by the following formula (1c):

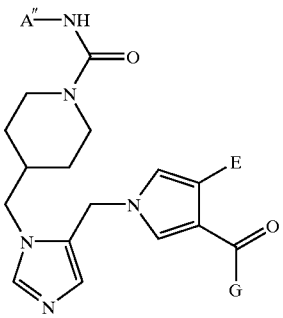

wherein A" is defined as previously described and E and G are defined as in claim 1; or (d) the compound of formula (1a) is reacted in a solvent in the presence of a reducing agent with a compound represented by the following formula (6):

D—CHO (6)

wherein D is defined as in claim 1, to produce a compound represented by the following formula (1d):

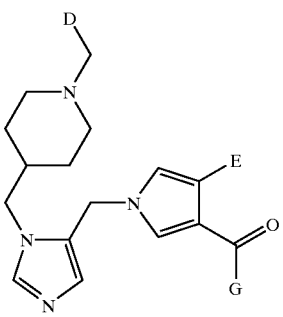

wherein D, E and G are defined as in claim 1; or (e) the compound of formula (1a) is reacted in a solvent with phosgene and a compound represented by the following formula (7):

D'H (7)

wherein D' represents a radical selected from the following group:

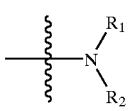 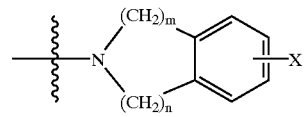

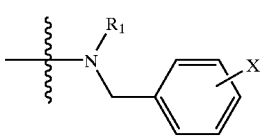

wherein m, n, X, R₁ and R₂ are defined as in claim 1, to produce a compound represented by the following formula (1e):

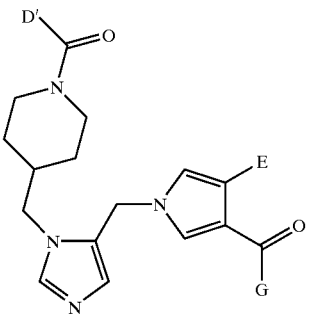

wherein D' is defined as previously described and E and G are defined as in claim 1.

5. A compound represented by the following formula (2):

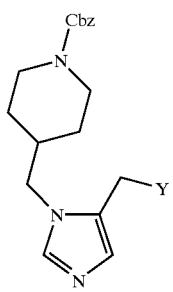

wherein Cbz represents benzyloxycarbonyl; and
Y represents hydroxy or chloro.

6. A process for preparing the compound of formula (2) as defined in claim 5 wherein (f) a compound represented by the following formula (8):

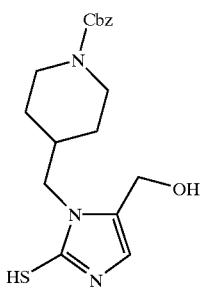

is desulfurized in an organic solvent in the presence of nitric acid to produce a compound represented by the following formula (2b):

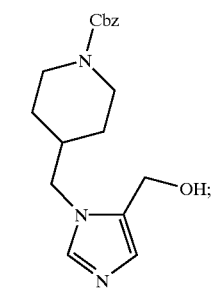

or (g) the compound of formula (2b) is with thionyl chloride (SOCl₂) to produce a compound represented by the following formula (2a)

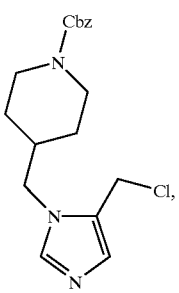

wherein Cbz represents benzyloxycarbonyl.

7. A pharmaceutical composition for inhibiting Ras farnesyl transferase activity in a mammalian which comprises a pharmaceutically acceptable carrier and as active ingredient a therapeutically effective amount of a compound of formula (1) as defined in claim 1 or a pharmaceutically acceptable salt thereof.

8. The pharmaceutical composition of claim 7 useful for treating or preventing cancer.

9. The pharmaceutical composition of claim 7 useful for treating or preventing restenosis.

10. The pharmaceutical composition of claim 7 useful for treating or preventing atherosclerosis.

11. The pharmaceutical composition of claim 7 useful for treating or preventing infections from hepatitis delta and related viruses.

* * * * *